United States Patent [19]

Hübsch et al.

[11] Patent Number: 4,992,462
[45] Date of Patent: Feb. 12, 1991

[54] SUBSTITUTED PYRROLES

[75] Inventors: Walter Hübsch; Rolf Angerbauer; Peter Fey; Hilmar Bischoff, all of Wuppertal; Dieter Petzinna, Duesseldorf; Delf Schmidt, Wuppertal, all of Fed. Rep. of Germany; Günter Thomas, Arese, Italy

[73] Assignee: Bayer Aktiengesellschaft, Leverkusen, Fed. Rep. of Germany

[21] Appl. No.: 178,956

[22] Filed: Apr. 7, 1988

[30] Foreign Application Priority Data

Apr. 14, 1987 [DE] Fed. Rep. of Germany ....... 3712720
Aug. 10, 1987 [DE] Fed. Rep. of Germany ....... 3726528
Nov. 13, 1987 [IT] Italy ............................. 22636 A/87

[51] Int. Cl.$^5$ .................... A61K 31/40; C07D 405/06
[52] U.S. Cl. .................................. 514/428; 514/422; 548/517; 548/562; 544/238; 544/237; 544/235; 544/405
[58] Field of Search ............... 548/562, 517; 514/422, 514/428

[56] References Cited

U.S. PATENT DOCUMENTS

| | | | |
|---|---|---|---|
| 4,248,873 | 2/1981 | Bossert et al. | 514/252 |
| 4,613,610 | 9/1986 | Wareing | 514/406 |
| 4,647,576 | 3/1987 | Hoefle | 548/562 |
| 4,661,483 | 4/1987 | Hoffman | 548/517 |
| 4,681,893 | 7/1987 | Roth | 514/422 |
| 4,694,018 | 9/1987 | Chinn | 548/562 |
| 4,735,958 | 5/1988 | Roth | 514/422 |
| 4,789,682 | 12/1988 | Stokker | 514/422 |
| 4,792,568 | 12/1988 | Auerbach | 548/562 |
| 4,795,811 | 3/1989 | Graham | 548/517 |
| 4,808,621 | 4/1989 | Roth et al. | 548/217 |
| 4,851,427 | 7/1989 | Wareing | 548/517 |
| 4,902,709 | 2/1990 | Stokker | 514/428 |

FOREIGN PATENT DOCUMENTS 0221025 5/1987 European Pat. Off. .
0300278 1/1989 European Pat. Off. ............ 548/562

OTHER PUBLICATIONS

Translation of German Application No. P 37 12720.9 filed 4/14/87.
Chem. Abstr., vol. 111, entry 115022m (1989), abstracting DE 3,722 806.
Burger, A., "Medicinal Chemistry", 2nd Ed., Interscience, N.Y., N.Y., (1960).

*Primary Examiner*—Donald G. Daus
*Attorney, Agent, or Firm*—Sprung Horn Kramer & Woods

[57] ABSTRACT

For inhibiting 3-hydroxy-3-methyl-glutaryl coenzyme A (HMG-CoA) reductase, the novel substituted pyrroles of the formula

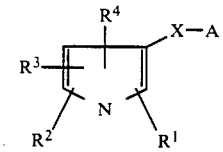

in which
  $R^1$ is optionally alkyl or cycloalkyl,
  $R^2$ and $R^3$ each is optionally substituted aryl or heteroaryl,
  $R^4$ is H or an organic radical,
  X is —CH$_2$—CH$_2$— or —CH=CH—,
  A is

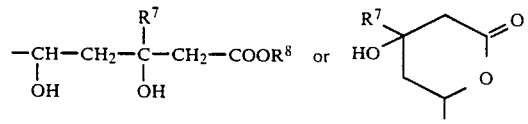

$R^7$ is H or alkyl, and
  $R^8$ is H or an ester or cation radical.

Novel intermediates therefor are also provided.

9 Claims, No Drawings

SUBSTITUTED PYRROLES

This invention relates to substituted pyrroles, intermediates for their preparation, their preparation and their use in medicaments.

It is known that lactone derivatives isolated from fungal cultures are inhibitors of 3-hydroxy-3-methylglutaryl coenzyme A reductase (HMG-CoA reductase) [mevinolin, EP No. 22,478; U.S. Pat. No. 4,231,938]. Certain indole derivatives and pyrazole derivatives are moreover also inhibitors of HMG-CoA reductase [EP-A- No.1,114,027; and U.S. Pat. No. 4,613,610].

Surprisingly, there have now been found substituted pyrroles which exhibit a good inhibitory action on HMG-CoA reductase (3-hydroxy-3-methyl-glutaryl coenzyme A reductase and cause a reduction in the blood cholesterol content, of the general formula (I)

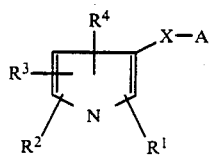
(I)

in which
$R^1$ represents cycloalkyl, or represents alkyl, which can be substituted by halogen, cyano, alkoxy, alkylthio, alkylsulphonyl, trifluoromethyl, trifluoromethoxy, trifluoromethylthio, trifluoromethylsulphonyl, alkoxycarbonyl or acyl or by a group of the formula —$NR^5R^6$,
wherein $R^5$ and $R^6$ are identical or different and denote alkyl, aryl, aralkyl, acyl, alkylsulphonyl or arylsulphonyl, or by carbamoyl, dialkylcarbamoyl, sulphamoyl, dialkylsulphamoyl, heteroaryl, aryl, aryloxy, arylthio, arylsulphonyl, aralkoxy, aralkylthio or aralkylsulphonyl, it being possible for the heteroaryl and aryl radicals of the substituents last mentioned to be substituted by up to 3 identical or different substituent from the group comprising halogen, cyano, trifluoromethyl, trifluoromethoxy, alkyl, alkoxy, alkylthio and alkylsulphonyl, $R^2$ and $R^3$ are identical or different and represent heteroaryl, which can be substituted by up to 3 identical or different substituents from the group comprising halogen, alkyl, alkoxy, alkylthio, alkylsulphonyl, aryl, aryloxy, arylthio, arylsulphonyl, trifluoromethyl, trifluoromethoxy, trifluoromethylthio and alkoxycarbonyl, and a group of the formula —$NR^5R^6$,
wherein $R^5$ and $R^6$ have the abovementioned meaning, or $R^2$ and $R^3$ represent aryl, which can be substituted by up to 5 identical or different substituents from the group comprising alkyl, alkoxy, alkylthio, alkylsulphonyl, aryl, aryloxy, arylthio, arylsulphonyl, aralkyl, aralkoxy, aralkylthio, aralkylsulphonyl, halogen, cyano, nitro, trifluoromethyl, trifluoromethoxy, trifluoromethylthio, alkoxycarbonyl, sulphamoyl, dialkylsulphamoyl, carbamoyl and dialkylcarbamoyl and a group of the formula —$NR^5R^6$,
wherein $R^5R^6$ have the abovementioned meaning, wherein $R^3$ also represents alkyl, $R^4$ represents hydrogen, or represents acyl, alkyl, sulphonyl or arylsulphonyl, it being possible for the aryl radical to be substituted by alkyl or halogen, or represents aminocarbonyl, alkylaminocarbonyl, dialkylaminocarbonyl, arylaminocarbonyl or alkoxycarbonyl, or represents cycloalkyl, or represents alkyl, which can be substituted by halogen, cyano, alkoxy, alkylthio, alkylsulphonyl, trifluoromethyl, trifluoromethoxy, trifluoromethylthio, trifluoromethylsulphonyl, alkoxycarbonyl or acyl or by a group of the formula —$NR^5R^6$,
wherein $R^5$ and $R^6$ are identical or different and denote alkyl, aryl, aralkyl, acyl, alkylsulphonyl or arylsulphonyl, or by carbamoyl, dialkylcarbamoyl, sulphamoyl, dialkylsulphamoyl, heteroaryl, aryl, aryloxy, arylthio, arylsulphonyl, aralkoxy, aralkylthio, or aralkylsulphonyl, it being possible for the heteroaryl and aryl radicals of the substituents last mentioned to be substituted by up to 3 identical or different substituents from the group comprising halogen, cyano, trifluoromethyl, trifluoromethoxy, alkyl, alkoxy, alkylthio and alkylsulphonyl, or $R^4$ represents heteroaryl, which can be substituted by up to 3 identical or different substituents from the group comprising halogen, alkyl, alkoxy, alkylthio, alkylsulphonyl, aryl, aryloxy, arylthio, arylsulphonyl, trifluoromethyl, trifluoromethoxy, trifluoromethylthio and alkoxycarbonyl and a group of the formula —$NR^5R^6$,
wherein $R^5$ and $R^6$ have the abovementioned meaning, or $R^4$ represents aryl, which can be substituted by up to 5 identical or different substituents from the group comprising alkyl, alkoxy, alkylthio, alkylsulphonyl, aryl, aryloxy, arylthio, arylsulphonyl, aralkyl, aralkoxy, aralkylthio, aralkylsulphonyl, halogen, cyano, nitro, trifluoromethyl, trifluoromethoxy, trifluoromethylthio, alkoxycarbonyl, sulphamoyl, dialkylsulphamoyl, carbamoyl and dialkylcarbamoyl and a group of the formula —$NR^5R^6$,
wherein $R^5$ and $R^6$ have the abovementioned meaning,
X represents a group of the formula —$CH_2$—$CH_2$— or —CH=CH— and
A represents a group of the formula

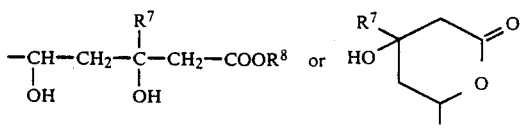

wherein
$R^7$ denotes hydrogen or alkyl and
$R^8$ denotes hydrogen, alkyl aryl, aralkyl have now been found.

In the foregoing definitions:

Cycloalkyl in general represents a cyclic hydrocarbon radical with 3 to 8 carbon atoms. The cyclopropane, cyclopentane and cyclohexane ring are preferred. Examples which may be mentioned are cyclopropyl, cyclopentyl, cyclohexyl, cycloheptyl and cyclooctyl.

Alkyl in general represents a straight-chain branched hydrocarbon radical with 1 to 12 carbon atoms. Lower alkyl with 1 to about 6 carbon atoms is preferred. Examples which may be mentioned are methyl, ethyl, propyl, isopropyl, butyl, isobutyl, pentyl, isopentyl, hexyl, isohexyl, heptyl, isoheptyl, octyl and isooctyl.

Alkoxy in general represents a straight-chain or branched hydrocarbon radical which has 1 to 12 carbon atoms and is bonded via an oxygen atom. Lower alkoxy with 1 to about 6 carbon atoms is preferred. An alkoxy radical with 1 to 4 carbon atoms is particularly preferred. Examples which may be mentioned are methoxy, ethoxy, propoxy, isopropoxy, butoxy, isobutoxy, pentoxy, isopentoxy, hexoxy, isohexoxy, heptoxy, isoheptoxy, octoxy and isooctoxy.

Alkylthio in general represents a straight-chain or branched hydrocarbon radical which has 1 to 12 carbon atoms and is bonded via a sulphur atom. Lower alkylthio with 1 to about 6 carbon atoms is preferred. An alkylthio radical with 1 to 4 carbon atoms is particularly preferred. Examples which may be mentioned are methylthio, ethylthio, propylthio, isopropylthio, butylthio, isobutylthio, pentylthio, isopentylthio, hexylthio, isohexylthio, heptylthio, isoheptylthio, octylthio and isooctylthio.

Alkylsulphonyl in general represents a straight-chain or branched hydrocarbon radical which has 1 to 12 carbon atoms and is bonded via an $SO_2$ group. Lower alkylsulphonyl with 1 to about 6 carbon atoms is preferred. Examples which may be mentioned are: methylsulphonyl, ethylsulphonyl, propylsulphonyl, isopropylsulphonyl, butylsulphonyl, isobutylsulphonyl, pentylsulphonyl, isopentylsulphonyl, hexylsulphonyl and isohexylsulphonyl.

Aryl in general represents an aromatic radical with 6 to about 12 carbon atoms. Preferred aryl radicals are phenyl, naphthyl and biphenyl.

Aryloxy in general represents an aromatic radical which has 6 to about 12 carbon atoms and is bonded via an oxygen atom. Preferred aryloxy radicals are phenoxy and naphthyloxy.

Arylthio in general represents an aromatic radical which has 6 to about 12 carbon atoms and is bonded via a sulphur atom. Preferred arylthio radicals are phenylthio and naphthylthio.

Arylsulphonyl in general represents an aromatic radical which has 6 to about 12 carbon atoms and is bonded via an $SO_2$ group. Examples which may be mentioned are: phenylsulphonyl, naphthylsulphonyl and biphenylsulphonyl.

Aralkyl in general represents an aryl radical which has 7 to 14 carbon atoms and is bonded via an alkylene chain. Aralkyl radicals with 1 to 6 carbon atoms in the aliphatic part and 6 to 12 carbon atoms in the aromatic part are preferred. The following aralkyl radicals may be mentioned as examples: benzyl, naphthylmethyl, phenethyl and phenylpropyl.

Aralkoxy in general represents an aralkyl radical with 7 to 14 carbon atoms, the alkylene chain being bonded via an oxygen atom. Aralkoxy radicals with 1 to 6 carbon atoms in the aliphatic part and 6 to 12 carbon atoms in the aromatic part are preferred. The following aralkoxy radicals may be mentioned as examples: benzyloxy, naphthylmethoxy, phenethoxy and phenylpropoxy.

Aralkylthio in general represents an aralkyl radical with 7 to about 14 carbon atoms, the alkyl chain being bonded via a sulphur atom. Aralkylthio radicals with 1 to 6 carbon atoms in the aliphatic part and 6 to 12 carbon atoms in the aromatic part are preferred. The following aralkylthio radicals may be mentioned as examples: benzylthio, naphthylmethylthio, phenethylthio and phenylpropylthio.

Aralkylsulphonyl in general represents an aralkyl radical with 7 to about 14 carbon atoms, the alkyl radicals being bonded via an $SO_2$ chain. Aralkylsulphonyl radicals with 1 to 6 carbon atoms in the aliphatic part and 6 to 12 carbon atoms in the aromatic part are preferred. The following aralkylsulphonyl radicals may be mentioned as examples: benzylsulphonyl, naphthylmethylsulphonyl, phenethylsulphonyl and phenylpropylsulphonyl.

Alkoxycarbonyl can be represented, for example, by the formula

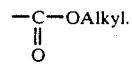

Alkyl here represents a straight-chain or branched hydrocarbon radical with 1 to 12 carbon atoms. Lower alkoxycarbonyl with 1 to about 6 carbon atoms in the alkyl part is preferred. Alkoxycarbonyl with 1 to 4 carbon atoms in the alkyl part is particularly preferred. The following alkoxycarbonyl radicals may be mentioned as examples: methoxycarbonyl, ethoxycarbonyl, propoxycarbonyl, isopropoxycarbonyl, butoxycarbonyl and isobutoxycarbonyl.

Acyl in general represents phenyl or straight-chain or branched lower alkyl which has 1 to about 6 carbon atoms, these radicals being bonded via a carbonyl group. Phenyl and alkyl radicals with up to 4 carbon atoms are preferred. Examples which may be mentioned are: benzoyl, acetyl, ethylcarbonyl, propylcarbonyl, isopropylcarbonyl, butylcarbonyl and isobutylcarbonyl.

Halogen in general represents fluorine, chlorine, bromine or iodine, preferably fluorine, chlorine or bromine. Halogen particularly preferably represents fluorine or chlorine.

Heteroaryl, in the context of the definition given above, in general represents a 5- to 6-membered aromatic ring which can contain oxygen, sulphur and/or nitrogen as hetero atoms and to which further aromatic rings can be fused. 5- and 6-membered aromatic rings which contain one oxygen, one sulphur and/or up to 2 nitrogen atoms and which are optionally benzo-fused are preferred. Particularly preferred heteroaryl radicals which may be mentioned are: thienyl, furyl, pyrrolyl, pyrazolyl, pyridyl, pyrimidyl, pyrazinyl, pyridazinyl, quinolyl, isoquinolyl, quinazolyl, quinoxalyl, phthalazinyl, cinnolyl, thiazolyl, benzothiazolyl, isothiazolyl, oxazolyl, benzoxazolyl, isoxazolyl, imidazolyl, benzimidazolyl, pyrazolyl, indolyl and isoindolyl.

If $R^8$ represents alkyl, aryl, aralkyl building up an ester radical, by this is preferably meant a physiologically tolerated ester radical which is readily hydrolyzed in vivo to give a free carboxyl group and a corresponding physiologically tolerated alcohol. These include, for example, alkyl esters ($C_1$ to $C_4$) and aralkyl esters ($C_7$ to $C_{10}$), preferably lower alkyl esters and benzyl esters. The following ester radicals may furthermore be mentioned: the methyl ester, ethyl ester, propyl ester and benzyl ester.

If $R^8$ represents a cation, by this is preferably meant a physiologically tolerated metal or ammonium cation. Cations which are preferred here are alkali metal and alkaline earth metal cations, such as, for example, sodium, potassium, magnesium or calcium cations, and aluminum or ammonium cations, as well as non-toxic substituted ammonium cations from amines, such as di-lower alkylamines, tri-lower alkylamines, procaine, dibenzylamine, N,N'-dibenzylethylenediamine, N-benzyl-β-phenylethylamine, N-methylmorpholine or N-ethylmorpholine, 1-ephenamine, dihydroabietylamine, N,N'-bis-dihydroabietylethylenediamine, N-lower alkylpiperidines and other amines which can be used to form salts.

The preferred substituted pyrroles correspond to the general formula

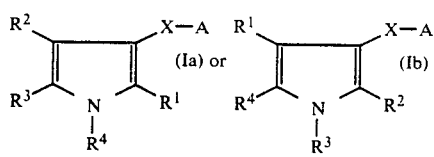

in which

R¹, R², R³, R⁴, X and A have the abovementioned meaning.

Preferred compounds are those of the general formula (Ia) and (Ib)

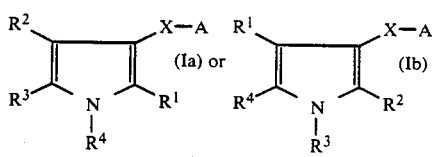

in which $R_1$ represents cyclopropyl, cyclopentyl or cyclohexyl, or represents lower alkyl, which can be substituted by pyridyl, Pyrimidyl, pyrazinyl, pyridazinyl, quinolyl, isoquinolyl, pyrrolyl, indolyl, thienyl, furyl, imidazoly, oxyzoly, thiazolyl, phenyl, phenoxy, phenylthio, phenylsulphonyl, benzyloxy, benzylthio, benzylsulphonyl, phenylethoxy, phenylethylthio or phenylethylsulphonyl, it being possible for the heteroaryl and aryl radicals mentioned to be substituted by up to 2 identical or different substituents from the group comprising fluorine, chlorine, bromine, lower alkyl, lower alkoxy, trifluoromethyl and trifluoromethoxy, by fluorine, chlorine, bromine, cyano, lower alkoxy, lower alkylthio, lower alkylsulphonyl, trifluoromethyl, trifluoromethoxy, trifluoromethylsulphonyl, lower alkoxycarbonyl, benzoyl or lower alkylcarbonyl or by a group of the formula —NR⁵R⁶,
wherein R⁵ and R⁶ are identical or different and denote lower alkyl, phenyl, benzlyl, acetyl, benzoyl, phenylsulphonyl or lower alkylsulphonyl, or R² and R³ are identical or different and represent thienyl, furyl, thiazolyl, isothiazolyl, oxazolyl, isoxazolyl, pyridyl, pyrimidyl, pyrazinyl, pyridazinyl, indolyl, isoindolyl, quinolyl, isoquinolyl, phthalazinyl, quinoxalinyl, quinazolinyl, cinnolinyl, benzothiazolyl, benzoxazolyl or benzimidazolyl, which can be substituted by up to 2 identical or different substituents from the group comprising fluorine, chlorine, bromine, lower alkyl, lower alkoxy, phenyl, phenoxy, trifluoromethyl, trifluoromethoxy and lower alkoxycarbonyl, or represent phenyl or naphthyl, which can be substituted by up to 4 identical or different substituents from the group comprising lower alkyl, lower alkoxy, lower alkylthio, lower alkylsulphonyl, phenyl, phenyloxy, phenylthio, phenylsulphonyl, benzyl, benzyloxy, benzylthio, benzylsulphonyl, phenethyl, phenylethoxy, phenylethylthio, phenylethylsulphonyl, fluorine, chlorine, bromine, cyano, trifluoromethyl, trifluoromethoxy, trifluoromethylthio and lower alkoxycarbonyl and a group of the formula —NR⁵R⁶, wherein 5 and R⁶ have the abovementioned meaning, R³ represents lower alkyl, R⁴ represents hydrogen, or represents benzoyl or lower alkylcarbonyl, or represents lower alkylsulphonyl, phenylsulphonyl or tolylsulphonyl, or represents aminocarbonyl, lower alkylaminocarbonyl, di-lower alkylaminocarbonyl, phenylaminocarbonyl or lower alkoxycarbonyl, or represents cyclopropyl, cyclopentyl or cyclohexyl, or represents lower alkyl, which can be substituted by fluorine, chlorine, bromine, cyano, lower alkoxy, lower alkylthio, lower alkylsulphonyl, trifluoromethyl, trifluoromethoxy, trifluoromethylsulphonyl, lower alkoxycarbonyl, benzoyl or lower alkylcarbonyl, or by a group of the formula
wherein R⁵ and R⁶ are identical or different and denote lower alkyl, phenyl, benzyl, acetyl, benzoyl, phenylsulphonyl or lower alkylsulphonyl, or by pyridyl, pyrimidyl, pyrazinyl, pyridazinyl, quinolyl, isoquinolyl, pyrrolyl, indolyl, thienyl, furyl, imidazolyl, oxazolyl, thiazolyl, phenyl, phenoxy, phenylthio, phenylsulphonyl, benzyloxy, benzylthio, benzylsulphonyl, phenylethoxy, phenylethylthio or phenylethylsulphonyl, it being possible for the heteroaryl and aryl radicals mentioned to be substituted by up to 2 identical or different substituents from the group comprising fluorine, chlorine, bromine, lower alkyl, lower alkoxy, trifluoromethyl and trifluoromethoxy, or R⁴ represents thienyl, furyl, thiazolyl, isothiazolyl, oxazolyl, isoxazolyl, pyridyl, pyrimidyl, pyrazinyl, pyridazinyl, indolyl, isoindolyl, quinolyl, isoquinolyl, phthalazinyl, quinoxalinyl, quinazolinyl, cinnolinyl, benzothiazolyl, benzoxazolyl or benzimidazolyl, which can be substituted by up to 2 identical or different substituents from the group comprising fluorine, chlorine, bromine, lower alkyl, lower alkoxy, phenyl, phenoxy, trifluoromethyl, trifluoromethoxy and lower alkoxycarbonyl, or represents phenyl or naphthyl, which can be substituted by up to 4 identical or different substituents from the group comprising lower alkyl, lower alkoxy, lower alkylthio, lower alkylsulphonyl, phenyl, phenyloxy, phenylthio, phenylsulphonyl, benzyl, benzyloxy, benzylthio, benzylsulphonyl, phenethyl, phenylethoxy, phenylethylthio, phenylethylsulphonyl, fluorine, chlorine, bromine, cyano, trifluoromethyl, trifluoromethoxy, trifluoromethylthio and lower alkoxycarbonyl and a group of the formula —NR⁵R⁶,
wherein R⁵ and R⁶ have the abovementioned meaning, X represents a group of the formula —CH₂—CH₂— or —CH=CH—, A represents a group of the formula

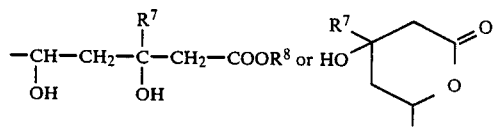

wherein

R⁷ denotes hydrogen or lower alkyl and

R⁸ denotes alkyl, aryl, aralkyl, or denotes a physiologically tolerated cation.

Particularly preferred compounds are those of the general formulae (Ia) and (Ib) in which R¹ represents cyclopropyl, cyclopentyl or cyclohexyl, or represents methyl, ethyl, propyl, isopropyl, butyl, sec.-butyl or tert.-butyl, which can be substituted by fluorine, chlorine, bromine, cyano, methoxy, ethoxy, propoxy, isopropoxy, butoxy, sec.-butoxy, tert.-butoxy, methylthio, ethylthio, propylthio, isopropylthio, methylsulphonyl, ethylsulphonyl, propylsulphonyl, isopropylsulphonyl, trifluoromethyl, trifluoromethoxy, methoxycarbonyl, ethoxycarbonyl, butoxycarbonyl, isobutoxycarbonyl, tert.-butoxycarbonyl, benzoyl, acetyl, pyridyl, pyrimidyl, thienyl, furyl, phenyl, phenoxy, phenylthio, phenylsulphonyl, benzyloxy, benzylthio or benzylsulphonyl, $R^2$ and $R^3$ are identical or different and represent pyridyl, pyrimidyl, quinolyl or isoquinolyl, which can be substituted by fluorine, chlorine, methyl, methoxy or trifluoromethyl, or represent phenyl, which can be substituted by up to 3 identical or different substituents from the group comprising methyl, ethyl, propyl, isopropyl, butyl, isobutyl, tert.-butyl, methoxy, ethoxy, propoxy, isopropoxy, butoxy, isobutoxy, tert.-butoxy, methylthio, ethylthio, propylthio, isopropylthio, methylsulphonyl, ethylsulphonyl, propylsulphonyl, isopropylsulphonyl, phenyl, phenoxy, benzyl, benzyloxy, fluorine, chlorine, bromine, cyano, trifluoromethyl, trifluoromethoxy, methoxycarbonyl, ethoxycarbonyl, propoxycarbonyl, isopropoxycarbonyl, butoxycarbonyl, isobutoxycarbonyl and tert.-butoxycarbonyl, wherein $R^3$ represents methyl, ethyl, propyl, isopropyl, butyl or isobutyl, $R^4$ represents hydrogen, cyclopropyl, cyclopentyl or cyclohexyl, or represents methyl, ethyl, propyl, isopropyl, butyl, Isobutyl, tert.-butyl, pentyl, isopentyl, hexyl or isohexyl, which can be substituted by fluorine, chlorine, bromine, cyano, methoxy, ethoxy, propoxy, isopropoxy, butoxy, isobutoxy, tert.-butoxy, methylthio, ethylthio, propylthio, isopropylthio, butylthio, isobutylthio, tert.-butylthio, methylsulphonyl, ethylsulphonyl, propylsulphonyl, isopropylsulphonyl, butylsulphonyl, isobutylsulphonyl, tert.-butylsulphonyl, trifluoromethyl, trifluoromethoxy, methoxycarbonyl, ethoxycarbonyl, propoxycarbonyl, isopropoxycarbonyl, butoxycarbonyl, isobutoxycarbonyl, tert.-butoxycarbonyl, benzoyl, acetyl or ethylcarbonyl, or by a group $-NR^5R^6$, wherein $R^5$ and $R^6$ are identical or different and denote methyl, ethyl, propyl, isopropyl, butyl, isobutyl, tert.-butyl, phenyl, benzyl, acetyl, methylsulphonyl, ethylsulphonyl, propylsulphonyl, isopropylsulphonyl or phenylsulphonyl, or by pyridyl, pyrimidyl, pyrazinyl, pyridazinyl, chinolyl, isoquinolyl, thienyl, furyl, phenyl, phenoxy, phenylthio, phenylsulphonyl, benzyloxy, benzylthio or benzylsulphonyl, it being possible for the heteroaryl and aryl radicals mentioned to be substituted by fluorine, chlorine, methyl, ethyl, propyl, isopropyl, isobutyl, tert.-butyl, methoxy, ethoxy, propoxy, isopropoxy, butoxy, isobutoxy, tert.-butoxy, trifluoromethyl or trifluoromethoxy, or $R^4$ represents thienyl, furyl, pyridyl, pyrimidyl, pyrazinyl, pyridazinyl, oxazolyl, isooxazolyl, imidazolyl, pyrazolyl, thiazolyl, isothiazolyl, quinolyl, isoquinolyl, benzoxazolyl, benzimidazolyl or benzothiazolyl, it being possible for the radicals mentioned to be substituted by fluorine, chlorine, methyl, ethyl, propyl, isopropyl, butyl, isobutyl, tert.-butyl, methoxy, ethoxy, propoxy, isopropoxy, butoxy, isobutoxy, tert.-butoxy, phenyl, phenoxy, trifluoromethyl, trifluoromethoxy, methoxycarbonyl, ethoxycarbonyl, isopropoxycarbonyl, propoxycarbonyl, butoxycarbonyl, isobutoxycarbonyl or tert.-butoxycarbonyl, or represents phenyl, which can be substituted by up to 3 identical or different substituents from the group comprising methyl, ethyl, propyl, isopropyl, butyl, isobutyl, tert.-butyl, pentyl, isopentyl, hexyl, isohexyl, methoxy, ethoxy, propoxy, isopropoxy, butoxy, isobutoxy, tert.-butoxy, methylthio, ethylthio, propylthio, isopropylthio, butylthio, isobutylthio, tert.-butylthio, methylsulphonyl, ethylsulphonyl, propylsulphonyl, isopropylsulphonyl, butylsulphonyl, isobutylsulphonyl, tert.-butylsulphonyl, phenyl, phenoxy, phenylthio, phenylsulphonyl, benzyl, benzyloxy, benzylthio, benzylsulphonyl, fluorine, chlorine, bromine, cyano, trifluoromethyl, trifluoromethoxy, trifluoromethylthio, methoxycarbonyl, ethoxycarbonyl, propoxycarbonyl, isopropoxycarbonyl, butoxycarbonyl, isobutoxycarbonyl and tert.-butoxycarbonyl and a group $-NR^5R^6$, wherein $R^5$ and $R^6$ have the abovementioned meaning, or $R^4$ represents benzoyl, acetyl, ethylcarbonyl, propylcarbonyl, isopropylcarbonyl, methylsulphonyl, ethylsulphonyl, propylsulphonyl, isopropylsulphonyl, butylsulphonyl, isobutylsulphonyl, tert.-butylsulphonyl, phenylsulphonyl or tolylsulphonyl, or represents aminocarbonyl, methyl-, ethyl-, propyl-, isopropyl-, butyl-, isobutyl- or tert.-butyl-aminocarbonyl, dimethyl-, diethyl-, dipropyl-, diisopropyl-, dibutyl- or diisobutylaminocarbonyl, phenylaminocarbonyl, methoxycarbonyl, ethoxycarbonyl, propoxycarbonyl, isopropoxycarbonyl, butoxycarbonyl, isobutoxycarbonyl or tert.-butoxycarbonyl, X represents a group of the formula $-CH_2-CH_2-$ or $-CH=CH-$ and A represents a group of the formula

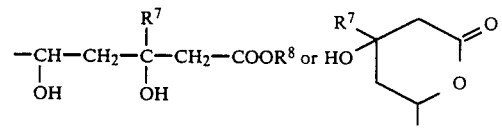

wherein $R^7$ denotes hydrogen, methyl, ethyl, propyl, isopropyl, butyl, isobutyl or tert.-butyl and $R^8$ denotes hydrogen, methyl, ethyl, propyl, isopropyl, butyl, isobutyl, tert.-butyl or benzyl, or denotes a sodium, potassium, calcium or magnesium ion or an ammonium ion.

The substituted pyrroles of the general formula (I) according to the invention have several asymmetric carbon atoms and can therefore exist in various stereochemical forms. The invention relates both to the individual isomers and to mixtures thereof.

Depending on the meaning of the group X or of the radical A, different stereoisomers result and are illustrated in more detail below:

(a) If the group $-X-$ represents a group of the formula $-CH=CH-$, the compounds according to the invention can exist in two stereoisomeric forms which can have the E-configuration (II) or the Z-configuration (III) on the double bond:

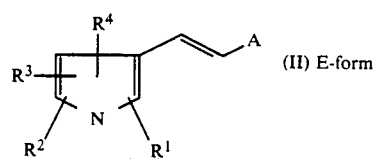

(II) E-form

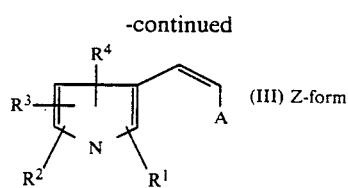 (III) Z-form ($R^1$ to $R^4$ and A have the abovementioned meaning).

Preferred compounds of the general formula (I) are those which have the E-configuration (II).

(b) If the radical —A— represents a group of the formula

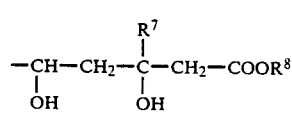

the compounds of the general formula (I) have at least two asymmetric carbon atoms, that is to say the two carbon atoms onto which the hydroxyl groups are bonded. Depending on the position of these hydroxyl groups in relation to one another, the compounds according to the invention can exist in the erythro-configuration (IV) or in the threo-configuration (V).

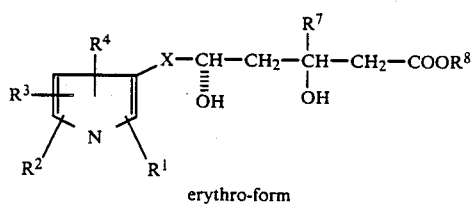 (IV)

erythro-form

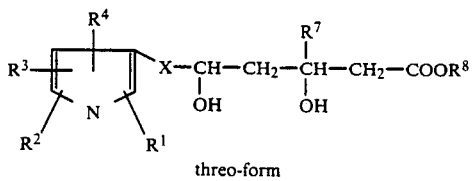 (V)

threo-form

In turn in each case two enantiomers both of the compounds in the erythro-configuration and in those of the threo-configuration exist, that is to say 3R,5S-isomers and 3S,5R-isomers (erythro-form) and 3R,5R-isomers and 3S,5S-isomers (threo-form).

The isomers in the erythro-configuration are preferred here, and the 3R,5S-isomer and the 3R,5S-3S,5R-racemate are particularly preferred.

(c) If the radical -A- represents a group of the formula

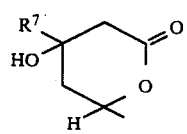

the substituted pyrroles have at least two asymmetric carbon atoms, that is to say the carbon atom to which the hydroxyl group is bonded and the carbon atom to which the radical of the formula

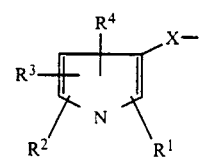

is bonded. Depending on the position of the hydroxyl group relative to the free valency on the lactone ring, the substituted pyrroles can exist as cis-lactones (VI) or as trans-lactones (VII).

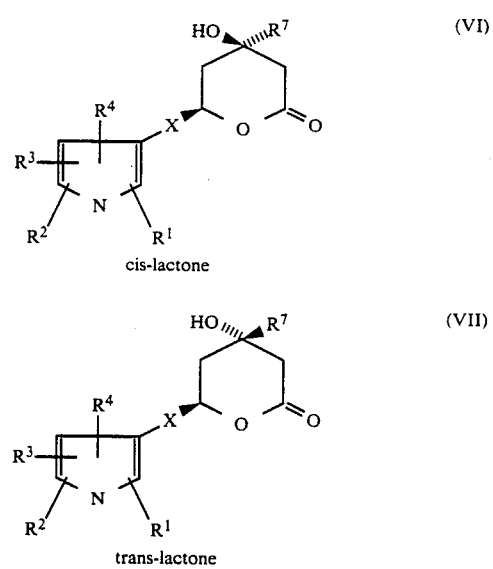

cis-lactone (VI)

trans-lactone (VII)

In turn in each case two isomers exist both of the cis-lactone and of the trans-lactone, that is to say the 4R,6R-isomer and the 4S,6S-isomer (cis-lactone), and the 4R,6S-isomer and 4S,6R-isomer (trans-lactone). Preferred isomers are the trans-lactones. The 4R,6S-isomer (trans) and the 4R,6S-4S,6R-racemate are particularly preferred here.

The following isomeric forms of the substituted pyrroles may be mentioned as examples:

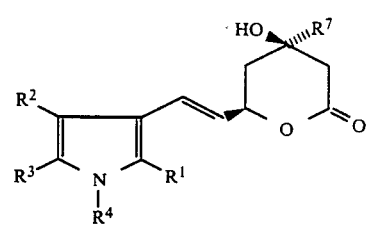

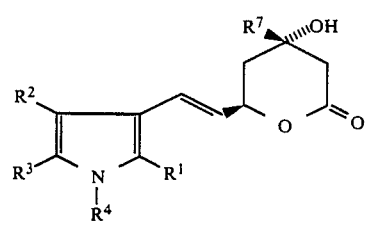

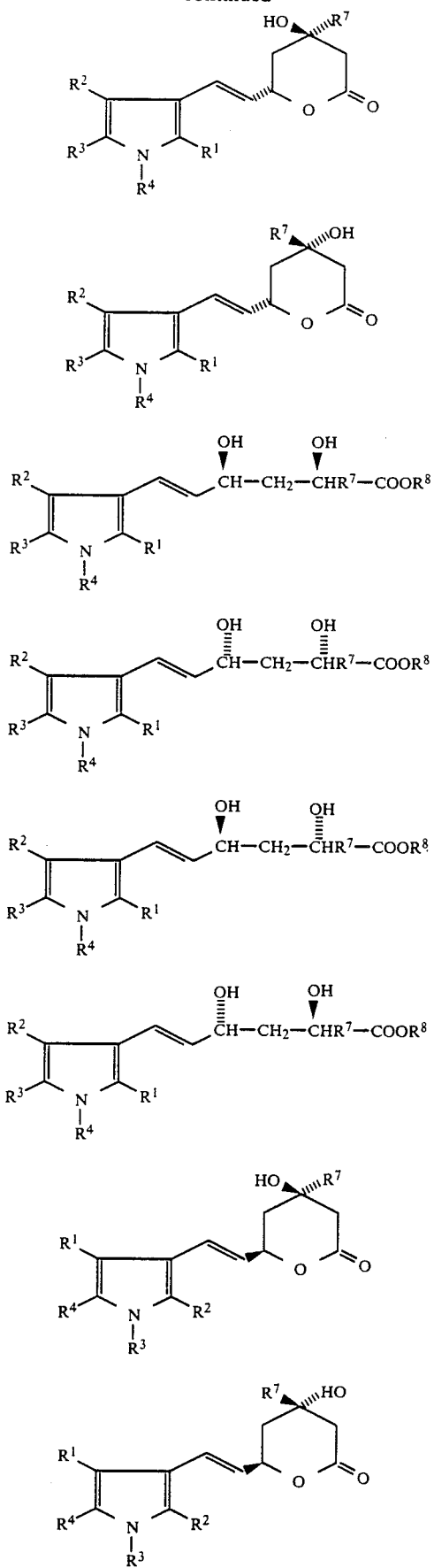
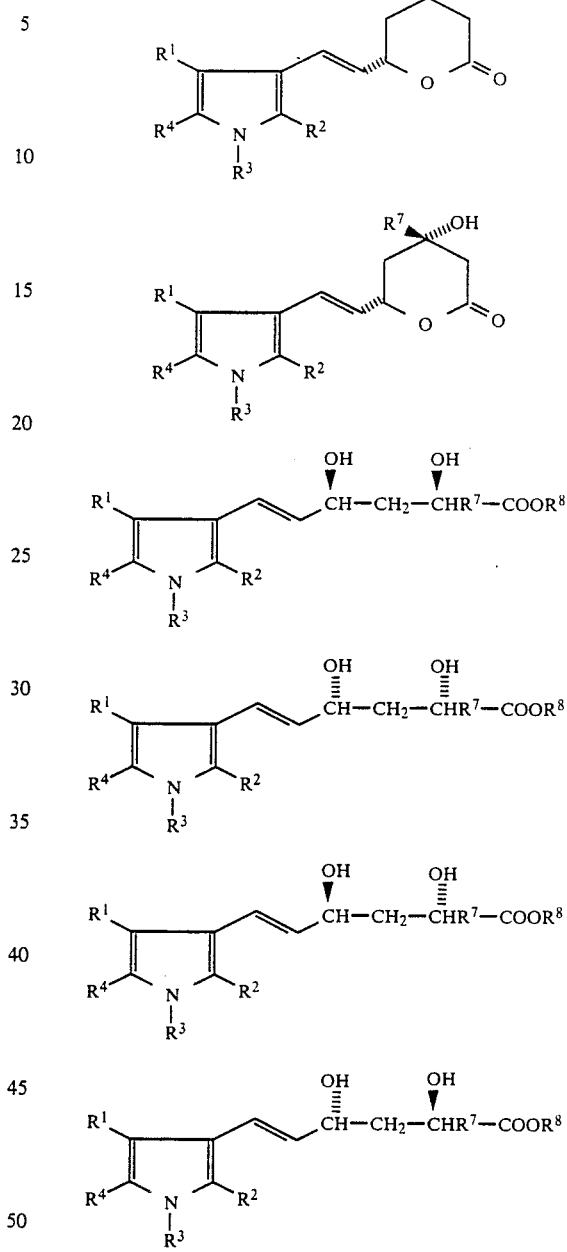

Especially preferred compounds are those of the general formula (Ia) and (Ib) in which $R^1$ represents cyclopropyl, methyl, ethyl, propyl, isopropyl, butyl, isobutyl or tert.-butyl, $R^2$ and $R^3$ are identical or different and represent phenly, which can be substituted by up to 2 identical or different substituents from the group comprising methyl, ethyl, propyl, isopropyl, methoxy, ethoxy, phenoxy, benzyloxy, fluorine, chlorine or trifluoromethyl, wherein $R^3$ represents methyl, ethyl, propyl or isopropyl, $R^4$ represents hydrogen, cyclopropyl, cyclopentyl or cyclohexyl, or represents methyl, ethyl, propyl, isopropyl, butyl, isobutyl, tert.-butyl, pentyl, isopentyl, hexyl or isohexyl, wherein $R^5$ and $R^6$ are identical or different and denote pyridyl, pyrimidyl, quinolyl, thienyl, furyl, phenyl, phenoxy, phenylsulphonyl or benzyloxy, optionally substituted by fluorine, chlorine, methyl, methoxy, trifluoromethyl or trifluoromethoxy or $R^4$ represents phenyl, which can be substituted by up to 2 identical or different substituents from the group comprising methyl, ethyl, methoxy, ethoxy, phenyl, benzyl, fluorine, chlorine, trifluoromethyl, X represents a group of the formula

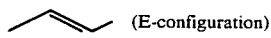 (E-configuration)

and

A represents a group of the formula

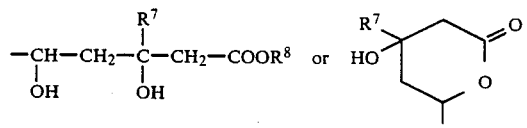

$R^7$ denotes hydrogen and $R^8$ denotes hydrogen, methyl or ethyl, or denotes a sodium or potassium cation.

A process has also been found for the preparation of the substituted pyrroles of the general formula (I)

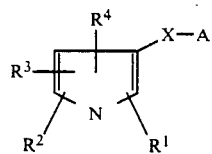 (I)

in which $R^1$, $R^2$, $R^3$, $R^4$, $R^5$, $R^6$, X and A have the abovementioned meaning, which is characterized in that ketones of the general formula (VIII)

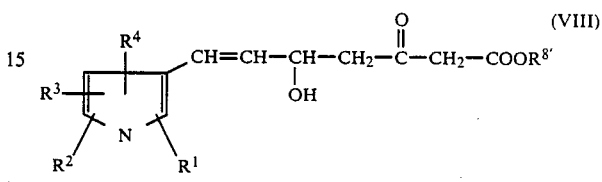 (VIII)

in which $R^1$, $R^2$, $R^3$ and $R^4$ have the abovementioned meaning and $R^{8'}$ represents alkyl, are reduced, in the case of preparation of the acids the esters are hydrolyzed, in the case of preparation of the lactones the carboxylic acids are cyclized, in the case of preparation of the salts either the esters or the lactones are hydrolyzed, in the case of preparation of the ethylene compounds (X=—CH₂—CH₂—) the ethene compounds (X=—CH=CH—) are hydrogenated by customary methods, and if appropriate isomers are separated.

The process according to the invention can be illustrated by the following equation:

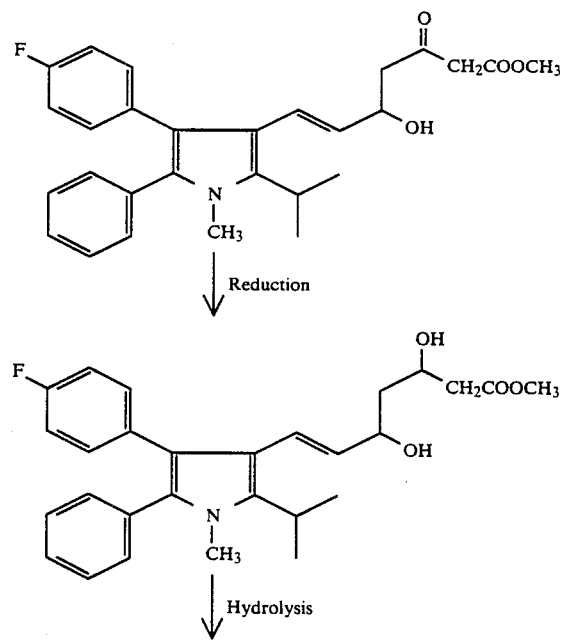

-continued

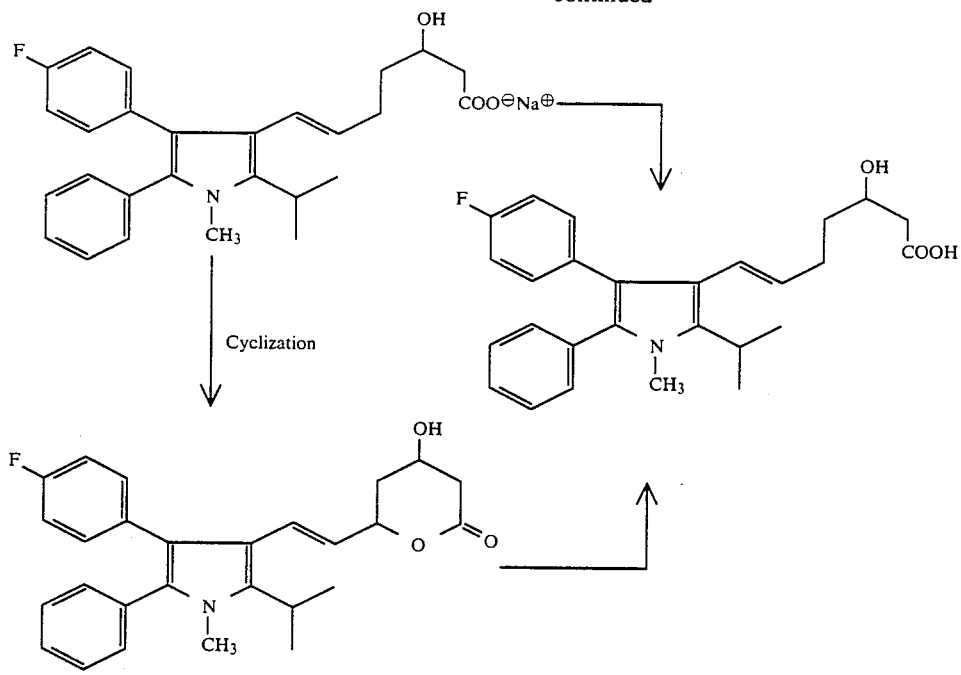

The reduction can be carried out with the customary reducing agents, preferably with those which are suitable for reduction of ketones to hydroxy compounds. Reduction with metal hydrides or complex metal hydrides in inert solvents, if appropriate in the presence of a trialkylborane, is particularly suitable here. The reduction is preferably carried out with complex metal hydrides, such as, for example, lithium boranate, sodium boranate, potassium boranate, zinc boranate, lithium trialkylhydrido-borates, sodium trialkyl-hydridoboranates, sodium cyano-trihydrido-borate or lithiumaluminum hydride. The reduction is especially preferably carried out with sodium borohydride in the presence of triethylborane.

Suitable solvents here are the customary organic solvents which do not change under the reaction conditions. These include, preferably, ethers, such as, for example, diethyl ether, dioxane, tetrahydrofuran or dimethoxyethane, or halogenohydrocarbons, such as, for example, methylene chloride, chloroform, carbon tetrachloride or 1,2-dichloroethane, or hydrocarbons, such as, for example, benzene, toluene or xylene. It is also possible to use mixtures of the solvents mentioned.

The reduction of the ketone group to the hydroxyl group is particularly preferably carried out under conditions under which the other functional groups, such as, for example, the alkoxycarbonyl group, are not changed. The use of sodium borohydride as the reducing agent in the presence of triethylborane in inert solvents, such as, preferably, ethers, is particularly suitable for this.

The reduction is in general carried out in a temperature range from −80° C. to room temperature, preferably from −78° C. to 0° C.

The process according to the invention is in general carried out at atmospheric pressure. However, it is also possible to carry out the process under reduced pressure or under increased pressure (for example in a range from 0.5 to 5 bar).

The reducing agent is in general used in an amount of 1 to 2 mols, preferably 1 to 1.5 mols, per mol of the keto compound.

Under the abovementioned reaction conditions, the carbonyl group is in general reduced to the hydroxyl group without reduction of the double bond to give a single bond taking place.

To prepare compounds of the general formula (I) in which X represents an ethylene grouping, the reduction of the ketones (III) can be carried out under those conditions under which both the carbonyl group and the double bond are reduced.

It is moreover also possible for the reduction of the carbonyl group and the reduction of the double bond to be carried out in two separate steps.

The carboxylic acids in the context of the general formula (I) correspond to the formula (Ic)

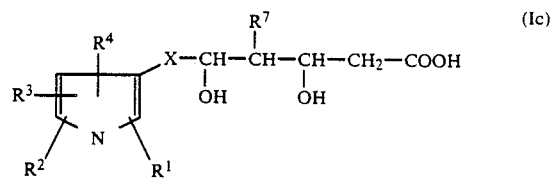

in which $R^1$, $R^2$, $R^3$, $R^4$, $R^7$ and X have the abovementioned meaning.

The carboxylic acid esters in the context of the general formula (I) correspond to the formula (Id)

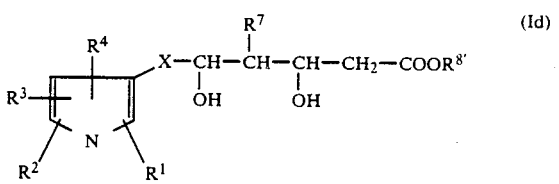

in which

R¹, R², R³, R⁴, R⁷ and X have the abovementioned meaning and

R⁸′ represents alkyl.

The salts of the compounds according to the invention in the context of the general formula (I) correspond to the formula (Ie)

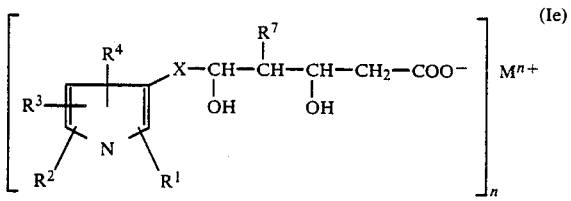

in which

R¹, R², R³, R⁴, R⁷ and X have the abovementioned meaning and $M^{n+}$ represents a cation.

The lactones in the context of the general formula (I) correspond to the formula (If)

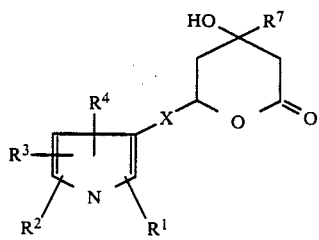

in which

R¹, R², R³, R⁴, R⁷ and X have the abovementioned meaning.

To prepare the carboxylic acids of the general formula (Ic) according to the invention, the carboxylic acid esters of the general formula (Id) or the lactones of the general formula (If) are in general hydrolyzed by customary methods. The hydrolysis is in general carried out by treating the esters or the lactones with customary bases in inert solvents, whereupon the salts of the general formula (Ie) are in general first formed and can then be converted into the free acids of the general formula (Ic) by treatment with acid in a second step.

Suitable bases for the hydrolysis are the customary inorganic bases. These include, preferably, alkali metal hydroxides or alkaline earth metal hydroxides, such as, for example, sodium hydroxide, potassium hydroxide or barium hydroxide, or alkali metal carbonates, such as sodium carbonate or potassium carbonate or sodium bicarbonate, or alkali metal alcoholates, such as sodium ethanolate, sodium methanolate, potassium methanolate, potassium ethanolate or potassium tert.-butanolate. Sodium hydroxide or potassium hydroxide are particularly preferably employed.

Suitable solvents for the hydrolysis are water or the organic solvents customary for hydrolysis. These include, preferably, alcohols, such as methanol, ethanol, propanol, isopropanol or butanol, or ethers, such as tetrahydrofuran or dioxane, or dimethylformamide or dimethylsulphoxide. Alcohols, such as methanol, ethanol, propanol or isopropanol, are particularly preferably used. It is also possible to use mixtures of the solvents mentioned.

The hydrolysis is in general carried out in a temperature range from 0° C. to +100° C., preferably from +20° C. to +80° C.

The hydrolysis is in general carried out at atmospheric pressure. However, it is also possible for the hydrolysis to be carried out under reduced pressure or under increased pressure (for example from 0.5 to 5 bar).

In carrying out the hydrolysis, the base is in general used in an amount of 1 to 3 mols, preferably 1 to 1.5 mols, per mol of the ester or lactone. Molar amounts of the reactants are particularly preferably used.

In carrying out the reaction, the salts of the compounds (Ie) according to the invention are formed as intermediate products in the first step and can be isolated. The acids (Ic) according to the invention obtained by treating the salts (Ie) with customary inorganic acids. These include, preferably, mineral acids, such as, for example, hydrochloric acid, hydrobromic acid, sulphuric acid or phosphoric acid. In the preparation of the carboxylic acids (Ic), it has proved advantageous here for the basic reaction mixture of the hydrolysis to be acidified in a second step without the salts being isolated. The acids can then be isolated in the customary manner.

To prepare the lactones of the formula (If) according to the invention, the carboxylic acids (Ic) are in general cyclized by customary methods, for example by heating the corresponding acid in inert organic solvents, if appropriate in the presence of molecular sieve.

Suitable solvents here are hydrocarbons, such as benzene, toluene, xylene or petroleum fractions, or tetralin or diglyme or triglyme. Benzene, toluene or xylene is preferably employed. It is also possible to use mixtures of the solvents mentioned. Hydrocarbons, in particular toluene in the presence of a molecular sieve, are particularly preferably used.

The cyclization is in general carried out in a temperature range from −40° C. to +200° C., preferably from −25° C. to +50° C.

The cyclization is in general carried out at atmospheric pressure, but it is also possible for the process to be carried out under reduced pressure or under increased pressure (for example in a range from 0.5 to 5 bar).

The cyclization is moreover also carried out in inert organic solvents with the aid of cyclizing or dehydrating agents. Carbodiimides are preferably used here as dehydrating agents. N,N′-Dicyclohexylcarbodiimide paratoluenesulphonate, N-cyclohexyl-N′-[2-(N″-methylmorpholinium)ethyl]carbodiimide or N-(3-dimethylaminopropyl)-N′-ethylcarbodiimide hydrochloride are preferably used as the carbodiimides.

Suitable solvents here are the customary organic solvents. These include, preferably, ethers, such as diethyl ether, tetrahydrofuran or dioxane, or chlorohydrocarbons, such as methylene chloride, chloroform or carbon tetrachloride, or hydrocarbons, such as benzene, toluene, xylene or petroleum fractions. Chlorohydrocarbons, such as, for example, methylene chloride, chloroform or carbon tetrachloride, or hydrocarbons, such as benzene, toluene or xylene, or petroleum fractions are particularly preferred. Chlorohydrocarbons, such as, for example, methylene chloride, chloroform or carbon tetrachloride, are particularly preferably used.

The reaction is in general carried out in a temperature range from 0° C. to +80° C., preferably from +10° C. to +50° C.

In carrying out the cyclization, it has proved to be advantageous to use the cyclization method with the aid of carbodiimides as dehydrating agents.

The isomers are in general resolved into the stereoisomerically uniform constituents by customary methods such as are described, for example, by E. L. Eliel, Stereochemistry of Carbon Compounds, McGraw Hill, 1962. Resolution of the isomers at the racemic lactones or esters stage is preferred here. It is particularly preferable here for the racemic mixture of the erythro-esters (IV) to be converted, by treatment either with D-(+)-or L-(−)-α-methylbenzylamine by customary methods, into the diastereomeric dihydroxyamides (Ig)

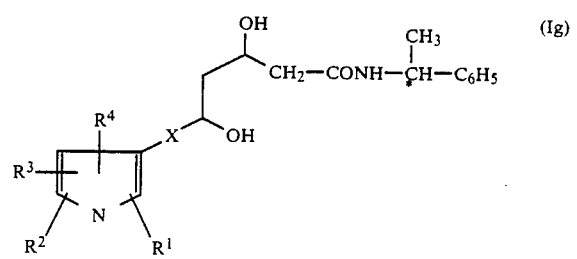

which can then be resolved into the individual diastereomers by chromatography or crystallization in the customary manner. Subsequent hydrolysis of the pure diastereomeric amides by customary methods, for example by treatment of the diastereomeric amides with inorganic bases, such as sodium hydroxide or potassium hydroxide, in water and/or organic solvents, such as alcohols, for example methanol, ethanol, propanol or isopropanol, gives the corresponding enantiomerically pure dihydroxy acids (Ic), which can be converted into the enantiomerically pure lactones by cyclization as described above. In general, for the preparation of the compounds of the general formula (I) according to the invention in enantiomerically pure form, the configuration of the end product obtained by the method described above depends on the configuration of the starting substances.

The resolution of isomers is illustrated by way of example in the following equation:

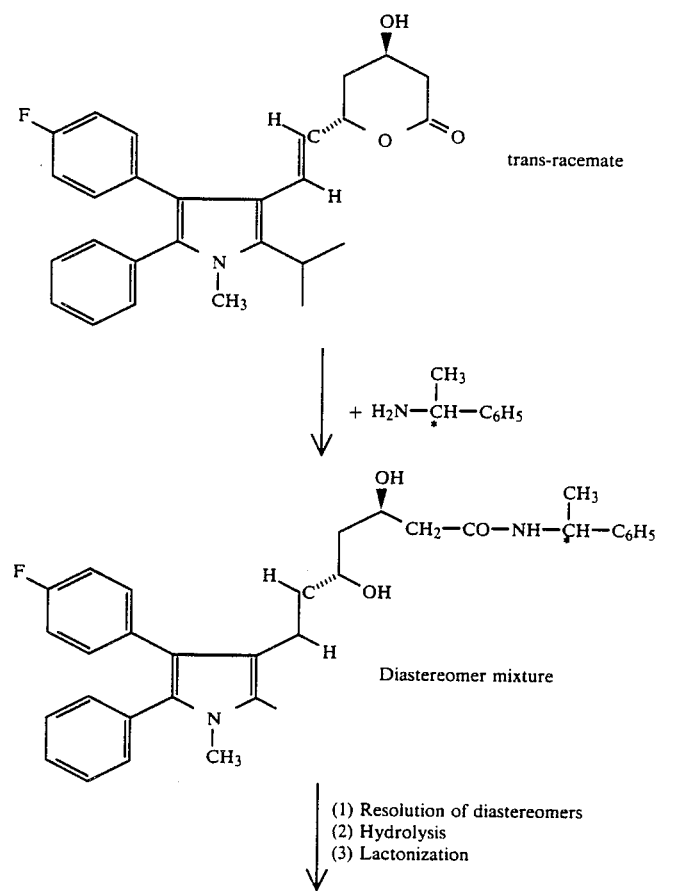

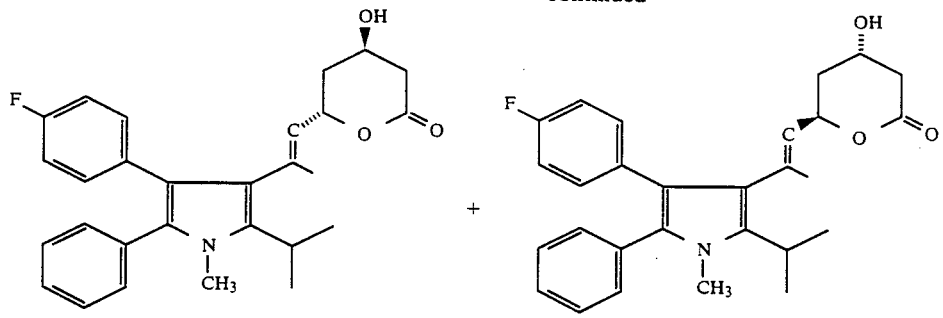

The ketones (VIII) used as starting substances are new.

A process has been found for the preparation of the ketones of the general formula (VIII) according to the invention

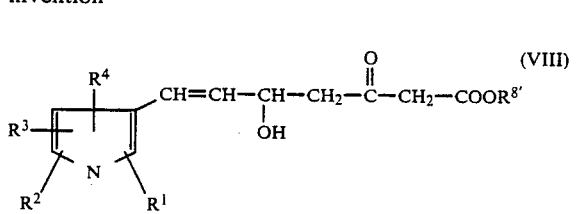

in which
$R^1$, $R^2$, $R^3$, $R^4$, $R^5$ and $R^6$ have the abovementioned meaning and
$R^{8'}$ represents alkyl,
which is characterized in that aldehydes of the general formula (IX)

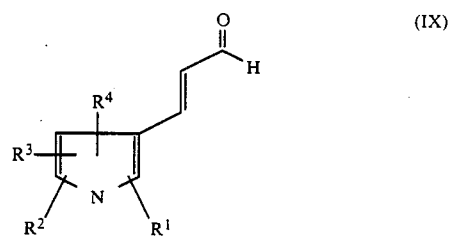

in which
$R^1$, $R^2$, $R^3$ and $R^4$ have the abovementioned meaning, are reacted with acetoacetic acid esters of the general formula (X)

in which
$R^{8'}$ has the abovementioned meaning, in inert solvents in the presence of bases.

The process according to the invention can be illustrated, for example, by the following equation:

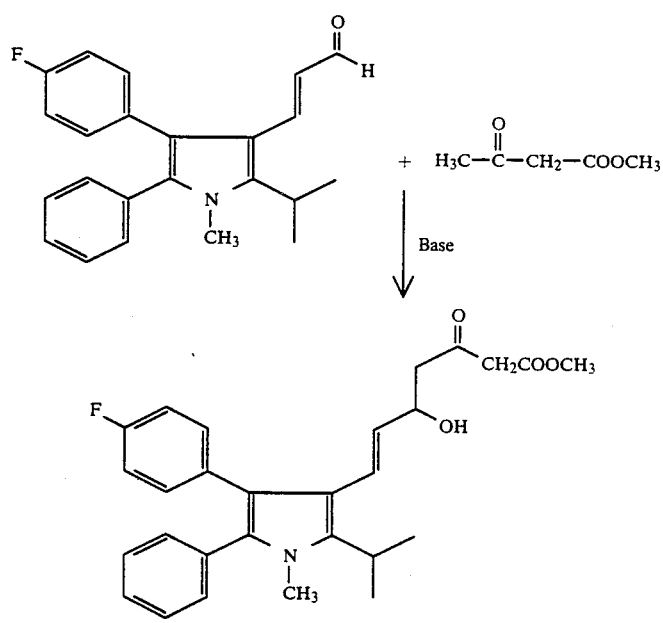

Possible bases here are the customary strongly basic compounds. These include, preferably, organolithium compounds, such as, for example, n-butyllithium, sec.- butyllithium, tert.-butyllithium or phenyllithium, or amides, such as, for example, lithium diisopropylamide, sodium amide or potassium amide, or lithium hexamethyldisilylamide, or alkali metal hydrides, such as sodium hydride or potassium hydride. It is also possible to use mixtures of the bases mentioned N-Butyllithium or sodium hydride or a mixture thereof is particularly preferably used.

Suitable solvents here are the customary organic solvents which do not change under the reaction conditions. These include, preferably, ethers, such as diethyl ether, tetrahydrofuran, dioxane or dimethoxyethane, or hydrocarbons, such as benzene, toluene, xylene, cyclohexane, hexane or petroleum fractions. It is also possible for mixtures of the solvents mentioned to be used. Ethers, such as diethyl ether or tetrahydrofuran, are particularly preferably used.

The reaction is in general carried out in a temperature range from $-80°$ C. to $+50°$ C., preferably from $-20°$ C. to room temperature.

The process is in general carried out at atmospheric pressure, but it is also possible for the process to be carried out under reduced pressure or under increased pressure, for example in a range from 0.5 to 5 bar.

In carrying out the process, the acetoacetic acid ester is in general used in an amount of 1 to 2, preferably 1 to 1.5 mols per mol of the aldehyde.

The acetoacetic acid esters of the formula (X) used as starting substances are known or can be prepared by known methods [Beilstein's Handbuch der organischen Chemie (Beilstein's Handbook of Organic Chemistry) III, 632; 438].

Examples which may be mentioned of acetoacetic acid esters for the process according to the invention are: methyl acetoacetate, ethyl acetoacetate, propyl acetoacetate and isopropyl acetoacetate.

The aldehydes Df the general formula (IX) used as starting substances are new.

A process has also been found for the preparation of the aldehydes of the general formula (IX)

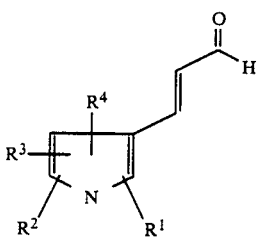

(IX)

in which $R^1$, $R^2$, $R^3$, $R^4$, $R^5$ and $R^6$ have the abovementioned meaning which is characterized in that pyrroles of the general formula (XI)

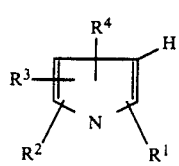

(XI)

in which $R^1$, $R^2$, $R^3$ and $R^4$ have the abovementioned meaning, are reacted with N,N-dimethylaminoacrolein of the formula (XII)

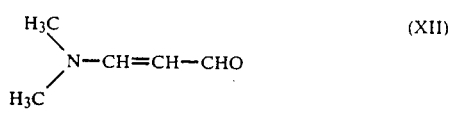

(XII)

in inert solvents in the presence of auxiliaries.

The process according to the invention can be illustrated, for example by the following equation:

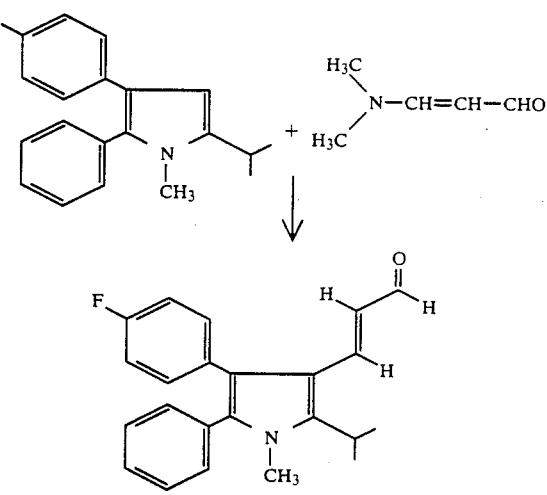

Suitable solvents here are the customary organic solvents which are stable under the reaction conditions. These include, preferably, hydrocarbons, such as benzene, toluene, xylene, hexane, petroleum fractions, chlorobenzene or dichlorobenzene, or ethers, such as diethyl ether, dioxane or tetrahydrofuran, or chlorohydrocarbons, such as methylene chloride, chloroform or carbon tetrachloride, or acetonitrile. It is also possible for mixtures of the solvents mentioned to be employed. Anhydrous acetonitrile or chloroform is particularly preferably used.

The auxiliaries used are in general acid chlorides. Phosphorus oxychloride or phosgene is preferably used, and phosphorus oxychloride is particularly preferred.

The reaction is carried out in a temperature range from $-20°$ C. to $+150°$ C., preferably from $0°$ C. to $+100°$ C.

The process is in general carried out at atmospheric pressure. However, it is also possible for the process to be carried out under reduced pressure or under increased pressure (for example in a range from 0.5 to 5 bar).

In carrying out the process, the dimethylaminoacrolein is in general employed in an amount of 2 to 6, preferably 3 to 4 mols per mol of the pyrrole.

The pyrroles of the general formula (XI) used as starting substances are known or can be prepared by known methods [A. Glossauer "Die Chemie der Pyrrole" ("The Chemistry of the Pyrroles"), Springer Verlag Berlin, 1974].

The compounds of the general formula (I) according to the invention have useful pharmacological properties, and in particular they are inhibitors of 3-hydroxy-3-methyl-glutaryl coenzyme A (HGM-CoA) reductase and as a result inhibitors of cholesterol biosynthesis. They can therefore be used for the treatment of hyperlipoproteinaemia, lipoproteinaemia or atherosclerosis. In addition the active compounds according to the invention cause a reduction in the blood cholesterol content.

The new active compounds can be converted in a known manner into the customary formulations, such as tablets, dragees, pills, granules, aerosols, syrups, emulsions, suspensions and solutions, using inert non-toxic pharmaceutically suitable excipients or solvents. The therapeutically active compound should in each case be present here in a concentration of about 0.5 to 98% by weight, preferably 1 to 90% by weight of the total mixture, that is to say in amounts which are sufficient to achieve the stated dosage range.

The formulations are prepared, for example, by extending the active compounds with solvents and/or excipients, if appropriate using emulsifying agents and/or dispersing agents, and, for example, in the case of the use of water as the diluent, organic solvents can be used as auxiliary solvents if appropriate.

Examples of auxiliaries which may be mentioned are: water, non-toxic organic solvents, such as paraffins (for example petroleum fractions), vegetable oils (for example groundnut oil/sesame oil), alcohols (for example ethyl alcohol or glycerol), excipients, such as, for example, natural rock powders (for example kaolins, aluminas, talc and chalk), synthetic rock powders (for example highly disperse silicic acid and silicates), sugars (for example sucrose, lactose and glucose), emulsifying agents (for example polyoxyethylene fatty acid esters, polyoxyethylene fatty alcohol ethers, alkylsulphonates and arylsulphonates), dispersing agents (for example lignin-sulphite waste liquors, methylcellulose, starch and polyvinylpyrrolidone) and lubricants (for example magnesium stearate, talc, stearic acid and sodium laurylsulphate).

Administration is effected in the customary manner, preferably orally, parenterally, perlingually or intravenously. In the case of oral use, tablets can of course also contain, in addition to the excipients mentioned, additives, such as sodium citrate, calcium carbonate and dicalcium phosphate, together with various additional substances, such as starch, preferably potato starch, gelatine and the like. Lubricants, such as magnesium stearate, sodium lauryl sulphate and talc, can furthermore be co-used for tablet making. In the case of aqueous suspensions, various flavor improvers or colorants can be added to the active compounds, in addition to the abovementioned auxiliaries.

In the case of parenteral use, solutions of the active compounds can be employed, using suitable liquid excipients.

In general, it has proved advantageous in the case of intravenous administration to administer amounts of about 0.001 to 1 mg/kg, preferably about 0.01 to 0.5 mg/kg of body weight to achieve effective results, and in the case of oral administration the dosage is about 0.01 to 20 mg/kg, preferably 0.1 to 10 mg/kg of body weight.

Nevertheless, it may at times be necessary to deviate from the amounts mentioned, and in particular to do so as a function of the body weight or nature of the administration route, of the individual behavior towards the medicament, of the nature of its formulation and the time or interval at which administration takes place. Thus, in some cases it may suffice to manage with less than the abovementioned minimum amount, while in other cases the upper limit mentioned must be exceeded. Where relatively large amounts are administered, it may be advisable to divide these into several individual doses over the course of the day.

PREPARATION EXAMPLES

EXAMPLE 1

1-(4-Fluorophenyl)-4-methyl-pent-1-en-3-one

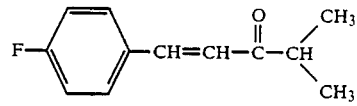

75 ml of 15% strength potassium hydroxide solution are added dropwise to 198.4 g (1.6 mols) of freshly distilled 4-fluorobenzaldehyde and 137.6 g (1.6 mols) of methyl isopropyl ketone in 300 ml of methanol and the mixture is stirred at room temperature overnight. It is then neutralized with 10 ml of acetic acid, 1 l of water is added and the mixture is extracted with two 500 ml portions of ether. The combined organic phases are washed with 500 ml of saturated sodium chloride solution and dried over sodium sulphate. After the solvent has been stripped off, the residue is distilled under a high vacuum.

Yield: 198.6 g (65% of theory) of yellowish oil.
Boiling point: 103° C. (0 3 mbar).
$^1$H-NMR (CDCl$_3$): $\delta$=1.2 (d, 6H, CH$_3$); 2.9 (septet, 1H, CH—(CH$_3$)$_2$); 6.8 (d, 1H, olefin-H); 7.1 (m, 2H, aromatic-H); 7.6 (m, 3H, aromatic-H +olefin-H).

EXAMPLE 2

2-(4-Fluorophenyl)-5-methyl-1-phenyl-hexane-1,4-dione

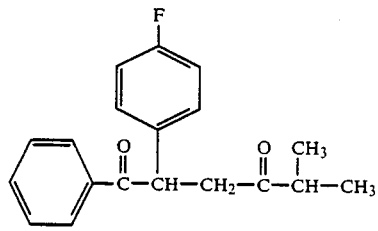

A solution of 63.6 g (0.6 mol) of freshly distilled benzaldehyde in 300 ml of dimethylformamide is added dropwise to a solution of 5.88 g (0.12 mol) of sodium cyanide in 300 ml of dimethylformamide at 35° C. in the course of 30 minutes and the mixture is stirred at this temperature for a further 5 minutes. 86.5 g (0.45 mol) of 1-(4-fluorophenyl)-4-methyl-pent-1-en-3-one (Example 1) in 500 ml of dimethylformamide are then added dropwise in the course of 1.5 hours and the mixture is subsequently stirred for 1 hour, the temperature always being kept at 35° C.

After 1 l of water has been added, the mixture is extracted four times with 400 ml of chloroform each time and the combined organic phases are washed with 1 l of saturated sodium bicarbonate solution and 1 l of water and dried over sodium sulphate. After concentration in vacuo, the residue is distilled under reduced pressure until, finally, a fraction passes over at 138°-142° C. (0.9 mbar). The distillation residue (132 g) is now chromatographed in two portions on a column (1.5 kg of silica gel 230–400 mesh, 0 9 cm), using petroleum ether/ethyl acetate (10:1). The product is obtained after 4–7 l of eluting agent. After the solvent has been stripped off, 90.0 g (67% of theory) of colorless oil remain.

¹H-NMR (CDCl₃): δ=1.08 (d, 3H, CH₃); 1.12 (d, 3H, CH₃); 2.65 (septet, 1H, CH—(CH₃)₂); 2.7 (dd, 1H, —CO—CH₂—CH); 3.6 (dd, 1H, —CO—CH₂—CH); 5.12 (dd, 1H, H—C—C₆H₄—F); 6.95 (m, 2H, aromatic-H); 7.23 (m, 2H, aromatic-H); 7.4 (m, 3H, aromatic-H); 7.95 (m, 2H, aromatic-H).

EXAMPLE 3

3-(4-Fluorophenyl)-5-isopropyl-1-methyl-2-phenyl-pyrrole

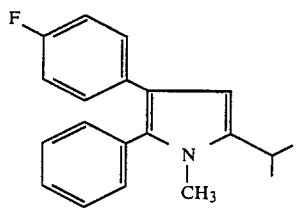

2.98 g (10 mmol) of 2-(4-fluorophenyl)-5-methyl1-phenyl-hexane-1,4-dione (Example 2) are heated at 80° C. in 10 ml of 40% strength aqueous methylamine solution, and about 14 ml of ethanol are added so that a clear solution forms. The solution is heated under reflux for a further 30 minutes and, after cooling, the precipitate is filtered off with suction. This is washed with a little ethanol and dried over phosphorus pentoxide in a vacuum desiccator.

Yield: 1.8 g (61% of theory) of colorless crystals.
Melting point: 114° C.

¹H-NMR (CDCl₃): δ=1.35 (d, 6H, CH—(CH₃)₂); 3.9 (septet, 1H, CH—(CH₃)₂); 3.42 (s, 3H, N—CH₃); 6.17 (s, 1H, pyrrole-H); 6.8–7.4 (m, 9H, aromatic-H).

EXAMPLE 4

(E)-3-[3-(4-Fluorophenyl)-5-isopropyl-1-methyl-2-phenyl-pyrrol-4-yl]prop-2-enal

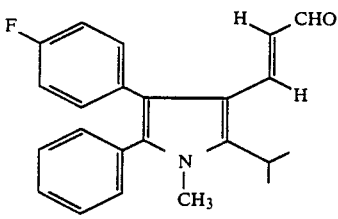

1.64 m( (18 mmol) of phosphorus oxychloride are taken in 10 ml of anhydrous acetonitrile. Under argon, a solution of 1.85 g (16.8 mmol) of 90% strength dimethylaminoacrolein in 7 ml of acetonitrile is first added dropwise at −10° C. to 0° C., and a solution of 1.76 g (6 mmol) of 3-(4-fluorophenyl)-5-isopropyl-1-methyl-2-phenyl-pyrrole (Example 3) in 7 ml of acetonitrile is then added at −5° C. to 0° C. The mixture is heated under reflux overnight. It is now added to a suspension of 4.4 g of sodium hydroxide in 65 ml of water and 65 ml of toluene at 10° C. such that the temperature does not rise above 25° C. After the mixture has been stirred at room temperature for 1.5 hours, it is filtered over kieselguhr and the phases are separated.

The organic phase is now dried over sodium sulphate and concentrated and the residue is chromatographed on a column (100 g of silica gel 230–400 mesh, 0 4 cm, methylene chloride). The purified product is finally boiled up in methanol.

Yield: 1.3 g (62% of theory) of yellowish solid.
Melting point: 215° C.

¹H—NMR (CDCl₃): δ=1.5 (d, 6H, CH—(CHHD 3)₂); 3.5 (m, 4H, N—CH₃+CH—(CH₃)₂); 5.8 (dd, 1H, olefin-H); 6.8–7.3 (m, 9H, aromatic-H); 7.6 (d, 1H, olefin-H); 9.4 (d, 1H, CHO).

EXAMPLE 5

Methyl (E)-7-[3′-(4″-fluorophenyl)-5′-isopropyl-1′-methyl-2′-phenyl-pyrrol-4′-yl]-5-hydroxy-3-oxo-hept-6-enoate

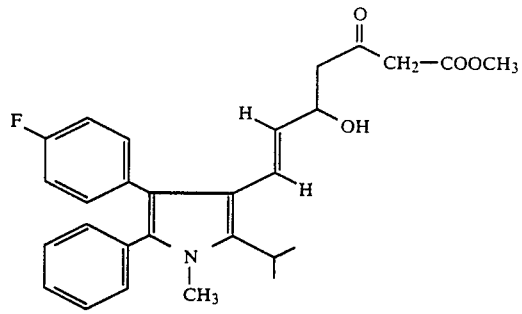

0.38 g (3.3 mmol) of methyl acetoacetate is added dropwise to a suspension of 0.11 g (3.6 mmol) of 80% strength sodium hydride in 10 ml of dry tetrahydrofuran at 0° C. under argon. After 15 minutes, 2.1 ml of 15% strength butyllithium in hexane are added dropwise at the same temperature in the course of 10 minutes and the mixture is subsequently stirred for 15 minutes. A solution of 1.04 g (3 mmol) of (E)-3-[3′-(4″-fluorophenyl)-5′-isopropyl-1′-methyl-2′-phenyl-pyrrol-4′-yl]-prop-2-enal (Example 4) in 15 ml of dry tetrahydrofuran is now added dropwise at 0° C. and the mixture is stirred at this temperature for a further 15 minutes. 15 ml of 0.6 N hydrochloric acid are then carefully added, the mixture is extracted three times with 15 ml of ether each time and the combined organic phases are washed with saturated sodium chloride solution and dried over sodium sulphate. After concentrating in vacuo, the residue is chromatographed in a column (50 g of silica gel 230–400 mesh, 0 3 cm) with toluene/ethyl acetate (5 : 1).

Yield: 0.58 g (42% of theory) of yellowish oil.

¹H—NMR (CDCl₃): δ=1.45 (d, 6H, CH—(CH₃)₂); 2.65 (m, 2H, —CH(OH)—CH₂—CO—); 3.45 (m, 5H, N—CH₃, CH₂—COCH₃); 3.73 (s, 3H, O—CH₃); 4.58 (m, 1H, HO—C—H); 5.2 (dd, 1H, olefin-H); 6.0 (d, 1H, olefin-H); 6.8–7.3 (m, 9H, aromatic—H).

EXAMPLE 6

Methyl erythro-(E)-7-[3-(4-fluorophenyl)-5-isopropyl-1-methyl-2-phenyl-pyrrol-4-yl]-3,5-dihydroxy-hept-6-enoate

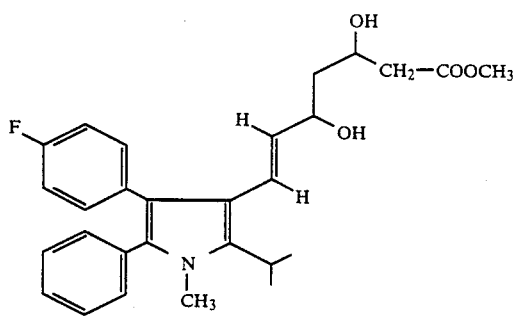

1.2 ml (1.2 mmol) of 1M triethylborane solution in hexane are added dropwise to a solution of 465 mg (1 mmol) of methyl (E)-7-[3'-(4''-fluorophenyl)-5'-isopropyl-1'-methyl- 2'-phenyl -pyrrol -4'-yl-]-5-hydroxy-3-oxo-hept-6-enoate (Example 5) in 15 ml of dry tetrahydrofuran at room temperature under argon, air is passed through the solution for 5 minutes and the mixture is then cooled to −78° C.

47 mg (1.24 mmol) of sodium borohydride are added, 0.6 ml of methanol is slowly added and the mixture is stirred at −78° C. for 15 minutes and at −30° C. for 15 minutes.

A solution of 3.3 ml of 30% strength hydrogen peroxide in 7 ml of water is then added dropwise at 0° C., the mixture is allowed to warm to room temperature and is extracted with 15 ml of ethyl acetate and the organic phase is washed with 10 ml each of 0.5 N hydrochloric acid and saturated sodium chloride solution and concentrated under reduced pressure. The residue (450 mg) is chromatographed on 80 g of silica gel 230–400 mesh in a column of 4 cm diameter using petroleum ether-/ethyl acetate (1:1).

Yield: 240 mg (52% of theory) of yellowish oil.

MS: m/e 465 (5%, M+), 447 (80%, M—H$_2$O).

$^1$H-NMR (CDCl$_3$): δ=1.45 (d, 6H, CH—(CH$_3$)$_2$); 1.6 (m, 2H, CH(OH)—CH$_2$—CHOH); 2.45 (m, 2H, CH$_2$—CO$_2$—CH$_3$); $\overline{2.6}$ (d, 1H, OH); 3.4 (septet, 1H, CH—(CH$_3$)$_2$); 3.5 (s, 3H, NCH$_3$); 3.6 (d, 1H, OH); 3.7 ($\overline{s, 3H}$, O—CH$_3$); 4.2 (m, 1H, OH—CH); 4.4 (m, 1H, HO—CH); 5.2 (dd, 1H, olefin-H); $\overline{6.6}$ (d, 1H, olefin-H); 6.8–7.3 (m, 9H, aromatic-H).

EXAMPLE 7

1-(4-Fluorophenyl)-4-methyl-pent-2-en-1-one

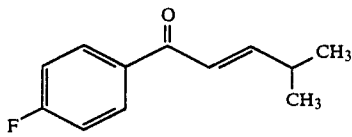

A solution of 17 g (0.3 mol) of potassium hydroxide in 125 ml of water/125 ml of methanol, warmed to 50° C., is added to 138.1 g (1.0 mol) of 4-fluoroacetophenone and 80 g (1.1 mols) of 2-methylpropanal are added dropwise during the course of 1.5 hours, whereupon a solid precipitates. After stirring for a further 3.5 hours at 50° C., the mixture is allowed to cool to 25° C., the solid is filtered off with suction, washed with 150 ml of methanol and, after drying, 132.3 g of dimeric condensation product are obtained. The solid is mixed with 5 g of sodium acetate and is distilled through a 20 cm Vigreux column in the water pump vacuum. A mixture (1:1.8) of 1-(4-fluorophenyl)-4-methyl-pent-2-en-1-one and 1-(4-fluorophenyl)4-methyl-pent-3-en-1-one is obtained.

Yield: 120.2 g (62% of theory).

Boiling point: 132° C. (14 mbar).

$^1$H-NMR (CDCl$_3$): δ=1.15 (d, 6H, CH$_3$); 1.7 (s, 3H, CH$_3$); 1.8 (s, 3H, CH$_3$); 2.6 (septet, 1H, CH—(CH$_3$)$_2$); 3.7 (d, 2H, CH$_2$—CH=C(CH$_3$)$_2$); $\overline{5.4}$ (m, 1H, CH$_2$—CH=C($\overline{CH_3}$)$_2$); 6.7 (d, 1H, olefin-H); 7.1 (dd, 1H, olefin-H); 7.2 (m, 4H, aromatic-H); 8.0 (m, 4H, aromatic-H).

EXAMPLE 8

1-(4-Fluorophenyl)-4-methyl-3-(1-nitroethyl)-pentan-1-one

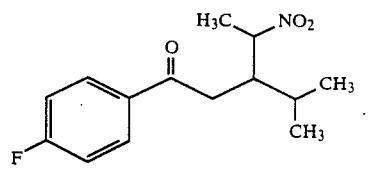

18.9 g (0.13 mol) of 1,5-diazabicyclo(5,4,0)undec-5-ene in 100 ml of acetonitrile are added dropwise at 0° C. to a solution of 50 g (0.26 mol) of the isomeric mixture (1:1.8) from Example 7 and 25 g (0.3 mol) of nitroethane in 150 ml of acetonitrile. After stirring for 2 hours at 25° C., 260 ml of 1 N hydrochloric acid are added and the mixture is extracted three times with dichloromethane. The combined organic phases are washed with 130 ml of 1 N hydrochloric acid, sodium bicarbonate solution and water, dried over sodium sulphate and concentrated in vacuo. 63 g of an oil are obtained, which is chromatographed on 800 g of silica gel with petroleum ether/ethyl acetate 10:1. Yield: 31 g (44% of theory) of oil as a diastereomeric mixture.

EXAMPLE 9

1-(4-Fluorophenyl)-3-isopropyl-pentan-1,4-dione

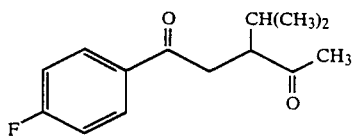

40 ml of 2 N sodium hydroxide solution are added to a solution of 18.7 g (70 mmol) of Example 8 in 120 ml of ethanol and this solution is added dropwise at 0° C. to 64 ml of 3 N sulphuric acid. After stirring for 1 hour at room temperature, the ethanol is removed in vacuo, the residue is taken up in water/dichloromethane, extracted three times with dichloromethane and the combined organic phases are washed with 1 N hydrochloric acid and also saturated sodium bicarbonate solution and water. The solution, which is dried over sodium sulphate, is concentrated in vacuo and the oil obtained (18.4 g) chromatographed on silica gel with petroleum ether/ethyl acetate (10:1).

Yield: 16 g (97% of theory).

$^1$H—NMR (CDCl$_3$): δ=0.9 (d, 3H, CH$_3$); 1.0 (d, 3H, CH$_3$); 2.1 (septet, 1H, C̲H(CH$_3$)$_2$); 2.3 (s, 3H, CH$_3$C═O); 2.9 (dd, 1H, CH$_2$—C═O); 3.1 (m, 1H, CH—C═O); 3.5 (dd, 1H, CH$_3$—C═O); 7.1 (m, 2H, aromatic-H); 8.0 (m, 2H, aromatic-H).

EXAMPLE 10

2-(4-Fluorophenyl)-5-methyl-1-phenyl-4-isopropyl-pyrrole

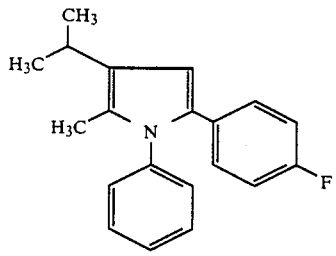

A solution of 25.3 g (0.11 mol) of Example 9, 70 g (0.75 mol) of aniline and a spatula tipful of p-toluene-sulphonic acid in toluene are heated under reflux overnight in a water separator. The solvent is then removed in vacuo and the residue (20.2 g) recrystallized from petroleum ether.

Yield: 7.1 g (22.5% of theory).

$^1$H-NMR (CDCl$_3$): δ=1.3 (d, 6H, (C̲H$_3$)$_2$CH); 2.1 (s, 3H, CH$_3$); 2.9 (septet, 1H, C̲H(CH$_3$)$_2$); 6.3 (s, 1H, pyrrole-H); 6.8 (m, 2H, aromatic-H); 7.0 (m, 2H, aromatic-H); 7.1 (m, 2H, aromatic-H); 7.4 (m, 3H, aromatic-H).

EXAMPLE 11

(E)-3-[2-(4-Fluorophenyl)-5-methyl-1-phenyl-4-isopropylpyrrol-3-yl]-prop-2-enal

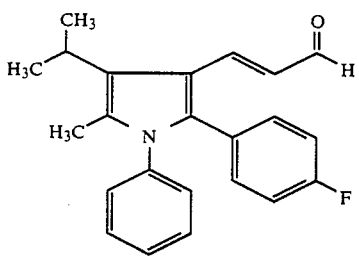

The compound mentioned above is obtained analogously to Example 4 from the compound from Example 10.

Yield: 82% of theory.

$^1$H-NMR (CDCl$_3$): δ=1.4 (d, 6H, (C̲H$_3$)$_2$CH); 2.1 (s, 3H, CH$_3$); 3.3 (septet, 1H, C̲H(CH$_3$)$_2$); 6.2 (dd, 1H, olefin-H); 6.9 (m, 2H, aromatic-H); 7.0 (m, 4H, aromatic-H); 7.3 (m, 3H, aromatic-H); 7.4 (d, 1H, olefin-H); 9.4 (d, 1H, CHO).

EXAMPLE 12

Methyl (E)-7-[2-(4-fluorophenyl)-5-methyl-1-phenyl-4-isopropyl-pyrrol-3-yl]-5-hydroxy-3-oxo-hept-6-enoate

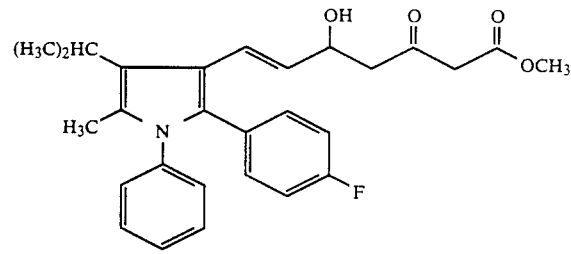

The compound mentioned above is obtained analogously to Example 5 from the compound from Example 11.

Yield: 0.7 g (35% of theory).

$^1$H-NMR (CDCl$_3$): δ=1.4 (d, 6H, (C̲H$_3$)$_2$CH); 2.1 (s, 3H, CH$_3$); 2.7 (m, 2H, CH(OH)C̲H$_2$); 3.2 (septet, 1H, C̲H(CH$_3$)2); 3.5 (s, 2H, C̲H$_2$COOCH$_3$); 3.7 (s, 3H, OCH$_3$); 4.6 (m, 1H, CHOH); 5.4 (dd, 1H, olefin-H); 6.5 (d, 1H, olefin-H); 6.8 (m, 2H, aromatic-H); 7.0 (m, 2H, aromatic-H); 7.2 (m, 5H, aromatic-H).

EXAMPLE 13

Methyl erythro-(E)-7-[2-(4-fluorophenyl)-5-methyl-1-phenyl-4-isopropyl-pyrrol-3-yl]-3,5-dihydroxy-hept-6-enoate

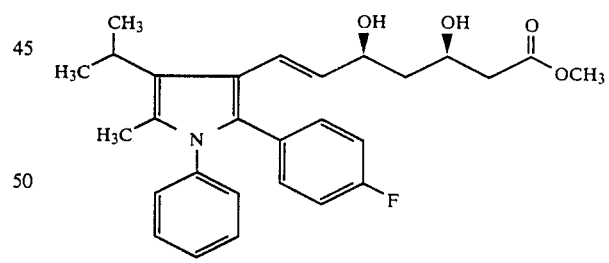

The compound mentioned above is obtained analogously to Example 6 from the compound from Example 12.

Yield: 0.42 g (69% of theory).

1H—NMR (CDCl$_3$): δ=1.4 (d, 6H, CH(C̲H$_3$)$_2$); 1.6 (m, 2H, CH$_2$—CHOH); 2.1 (s, 3H, CH$_3$); 2.5 (m, 2H, C̲H$_2$COOCH$_3$); 3.2 (septet, 1H, CH(CH$_3$)$_2$); 3.7 (s, 3H, OCH$_3$); 4.2 (m, 1H, CHOH); 4.4 (m, 1H, CHOH); 5.4 (dd, 1H, olefin-H); 6.5 (d, 1H, olefin-H); 6.8–7.3 (m, 9H, aromatic-H).

EXAMPLE 14

Methyl erythro-(E)-7-[1-(2,6-dimethylphenyl)-2-(4-fluorophenyl)-5-methyl-4-isopropyl-pyrrol-3-yl]-3,5-dihydroxyhept-6-enoate

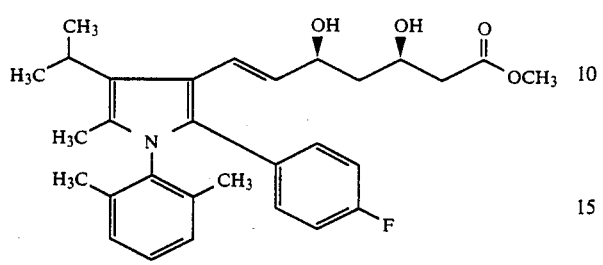

The compound mentioned above is obtained analogously to Example 13.
Yield: 67% of theory.
$^1$H-NMR (CDCl$_3$): δ=1.4 (d, 6H, (CH$_3$)$_2$CH); 1.6 (m, 2H, CH$_2$—CHOH); 2.0 (m, 9H, CH$_3$); 2.5 (m, 2H, CH$_2$COOCH$_3$); 3.2 (m, 1H, OH (CH$_3$)$_2$); 3.7 (s, 3H, OCH$_3$); 4.2 (m, 1H, CHOH); 4.4 (m, 1H, CHOH); 5.5 (dd, 1H, olefin-H); 6.5 (d, 1H, olefin-H); 6.7 - 7.3 (m, 7H, aromatic-H).

EXAMPLE 15

Methyl erythro-(E)-7-[1-benzyl-2-(4-fluorophenyl)-4-isopropyl-5-methyl-pyrrol-3-yl]-3,5-dihydroxy-hept-6-enoate

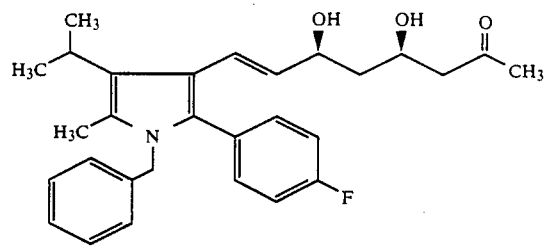

The compound mentioned above is obtained analogously to EXAMPLE 13.
Yield: 39% of theory.
$^1$H—NMR (CDCl$_3$): δ=1,3 (d, 6H, (CH$_3$)$_2$CH); 1.6 (m, 2H, CH$_2$CHOH); 2.1 (s, 3H, CH$_3$); 2.5 (m, 2H, CH$_2$COOCH$_3$); 3.1 (m, 1H, CH(CH$_3$)$_2$); 3.7 (s, 3H, OCH$_3$); 4.2 (m, 1H, CHOH); 4.3 (m, 1H, CHOH); 4.9 (s, 2H, CH$_2$Ph); 5.3 (dd, 1H, olefin-H); 6.5 (d, 1H, olefin-H); 6.7 - 7.3 (m, 9H, aromatic-H).

The compounds shown in Table 1 were obtained analogously to Example 15 and the reactions described in Examples 1-5.

TABLE 1

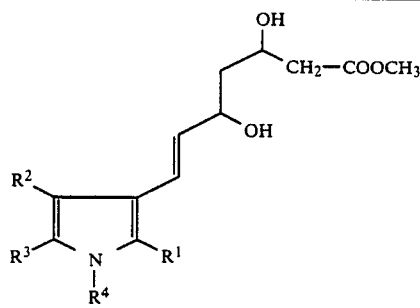

| Ex. No. | R$^1$ | R$^2$ | R$^3$ | R$^4$ | $^1$H-NMR [δ ppm, CDCl$_3$, 300 MHz] |
|---|---|---|---|---|---|
| 16 | —CH(CH$_3$)$_2$ | —phenyl | —phenyl | —CH$_3$ | 1.43 (d,6H); 1.6 (m,2H); 2.47 (m,2H); 3.39 (sept.,1H); 3.47 (s,3H); 3.72 (s 3H); 4.20 (m,1H); 4.38 (m,1H); 5.24 (dd, (1H); 6.60 (d,1H); 7.0–7.3 (m,10H). |
| 17 | —CH(CH$_3$)$_2$ | —(4-Cl-phenyl) | —phenyl | —CH$_3$ | 1.43 (d,6H); 1.6 (m,2H); 2.47 (m,2H); 3.34 (m,1H); 3.45 (s,3H); 3.72 (s,3H); 4.23 (m,1H); 4.38 (m,1H); 5.36 (dd,1H); 6.56 (d,1H); 6.90–7.30 (m,9H). |
| 18 | —CH(CH$_3$)$_2$ | —(4-CH$_3$-phenyl) | —phenyl | —CH$_3$ | 1.43 (d,6H); 1.6 (m,2H); 2.26 (s,3H); 2.47 (m,2H); 3.38 (sept.,1H); 3.47 (s,3H); 3.72 (s,3H); 4.22 (m,1H); 4.38 (m,1H); 5.28 (dd,1H); 6.57 (d,1H); 6.90–7.30 (m,9H). |
| 19 | —CH(CH$_3$)$_2$ | —(4-OCH$_3$-phenyl) | —phenyl | —CH$_3$ | 1.43 (d,6H); 1.6 (m,2H); 2.47 (m,2H); 3.38 (sept.,1H); 3.47 (s,3H); 3.71 (s, 3H); 3.76 (s,3H); 4.22 (m,1H); 4.37 (s, 1H); 5.27 (dd,1H); 6.57 (d, 1H); 6.70–7.30 (m,1H). |
| 20 | —CH(CH$_3$)$_2$ | —(2-F-phenyl) | —phenyl | —CH$_3$ | 1.43 (d,6H); 1.6 (m,2H); 2.44 (m,2H); 3.35 (sept.,1H); 3.48 (s,3H); 3.68 (s, 3H); 4.15 (m,1H); 4.35 (m,1H); 5.12 (dd, 1H); 6.62 (d, 1H); 6.9–7.3 (m, 9H). |

TABLE 1-continued

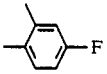

| Ex. No. | R¹ | R² | R³ | R⁴ | ¹H-NMR [δ ppm, CDCl₃, 300 MHz] |
|---|---|---|---|---|---|
| 21 | —CH(CH₃)₂ | 2,4-difluorophenyl | phenyl | —CH₃ | 1.43 (d,6H); 1.6 (m,2H); 2.47 (m,2H); 3.36 (sept., 1H); 3.48 (s,3H); 3.70 (s, 3H); 4.18 (m,1H); 4.35 (m,1H); 5.12 (dd, 1H); 6.61 (d, 1H); 6.70-7.30 (m,8H). |
| 22 | —CH(CH₃)₂ | 2-methyl-4-fluorophenyl | phenyl | —CH₃ | 1.43 (d,6H); 1.6 (m,2H); 1.98 (s,3H); 2.43 (m,2H); 3.34 (sept.,1H); 3.50 (s, 3H); 3.72 (s,3H); 4.11 (m,2H); 4.28 (m,2H); 4.94 (dd,1H); 6.60 (d, 1H); 6.70-7.30 (m,8H). |
| 23 | —CH(CH₃)₂ | 2-fluoro-3-phenoxyphenyl | phenyl | —CH₃ | 1.42 (d,6H); 1.6 (m,2H); 2.45 (m,2H); 3.34 (sept.,1H); 3.43 (s,3H); 3.72 (s, 3H); 4.22 (m,1H); 4.38 (m,1H); 5.27 (dd, 1H); 6.55 (d,1H); 6.70-7.35 (m,13H). |
| 24 | —C(CH₃)₃ | 4-fluorophenyl | phenyl | —CH₃ | 1.35 (m,2H); 1.52 (s,9H); 2.40 (m,2H); 3.57 (s,3H); 3.71 (s,3H); 4.10 (m,1H); 4.32 (m,1H); 4.95 (dd,1H); 6.70 (d,1H); 6.70-7.30 (m,9H). |
| 25 | cyclopropyl | 4-fluorophenyl | phenyl | —CH₃ | 0.71 (m,2H); 1.08 (m,2H); 1.67 (m,3H); 2.48 (m,2H); 3.57 (s,3H); 3.71 (s,3H); 4.27 (m,1H); 4.42 (m,1H); 5.63 (dd,1H); 6.52 (d,1H); 6.80-7.30 (m,9H). |
| 26 | —CH(CH₃)₂ | 4-fluorophenyl | 4-chlorophenyl | —CH₃ | 1.43 (d,6H); 1.6 (m,2H); 2.47 (m,2H); 3.36 (sept.,1H); 3.47 (s,3H); 3.72 (s, 3H); 4.21 (m,1H); 4.36 (m,1H); 5.20 (dd, 1H); 6.55 (d,1H); 6.80-7.20 (m,8H). |
| 27 | —CH(CH₃)₂ | 4-fluorophenyl | 4-fluorophenyl | —CH₃ | 1.43 (d,6H); 1.6 (m,2H); 2.48 (m,2H); 3.38 (sept.,1H); 3.47 (s,3H); 3.72 (s, 3H); 4.21 (m,1H); 4.38 (m,1H); 5.22 (dd,1H); 6.56 (d,1H); 6.70-7.20 (m,8H). |
| 28 | —CH(CH₃)₂ | phenyl | 3-(4-fluorobenzyloxy)phenyl | —CH₃ | 1.43 (d,6H); 1.6 (m,2H); 2.46 (m,2H); 3.38 (sept.,1H); 3.48 (s,3H); 3.72 (s, 3H); 4.18 (m,1H); 4.35 (m,1H); 4.78 (s, 2H); 5.23 (dd,1H); 6.57 (d,1H); 6.70-7.40 (m,13H). |
| 29 | —CH(CH₃)₂ | phenyl | 3-(3-fluorobenzyloxy)phenyl | —CH₃ | 1.43 (d,6H); 1.6 (m,2H); 2.47 (m,2H); 3.37 (sept.,1H); 3.48 (s,3H); 3.72 (s,3H); 4.19 (m,1H); 4.37 (m,1H); 4.85 (s,2H); 5.22 (dd,1H); 6.50-7.30 (m,14H). |
| 30 | —CH(CH₃)₂ | 4-fluorophenyl | 3-benzyloxyphenyl | —CH₃ | 1.43 (d,6H); 1.6 (m,2H); 2.47 (m,2H); 3.35 (sept.,1H); 3.44 (s,3H); 3.72 (s, 3H); 4.22 (m,1H); 4.38 (m,1H); 5.00 (s,2H); 5.22 (dd,1H); 6.57 (d,1H); 6.60-7.40 (m,13H). |
| 31 | —CH(CH₃)₂ | 4-fluorophenyl | phenyl | —CH₂CH₃ | 1.12 (t,3H); 1.43 (d,6H); 1.6 (m,2H); 2.47 (m,2H); 3.28 (sept.,1H); 3.72 (s, 3H); 3.83 (q,2H); 4.18 (m,1H); 4.36 (m, 1H); 5.13 (dd,1H); 6.58 (d,1H); 6.70-7.30 (m,9H). |

TABLE 1-continued

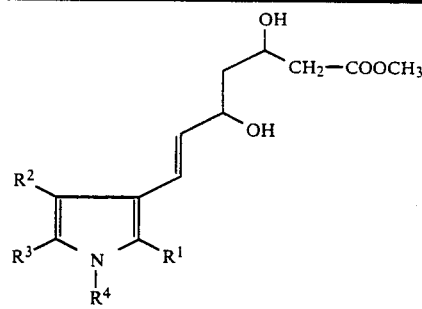

| Ex. No. | R¹ | R² | R³ | R⁴ | ¹H-NMR [δ ppm, CDCl₃, 300 MHz] |
|---|---|---|---|---|---|
| 32 | —CH(CH₃)₂ | ⌬—F | ⌬ | —CH(CH₃)₂ | 1.45 (m,12H); 1.6 (m,2H); 2.47 (m,2H); 3.42 (sept.,1H); 3.70 (s,3H); 4.17 (m, 1H); 4.33 (m,1H); 4.41 (m,1H); 5.06 (dd, 1H); 6.70 (d,1H); 6.70–7.30 (m,9H). |
| 33 | —CH(CH₃)₂ | ⌬—F | ⌬ | —H | 1.45 (d,6H); 1.6 (m,2H); 2.47 (m,2H); 3.30 (sept.,1H); 3.75 (s,1H); 4.22 (m, 1H); 4.37 (m,1H); 5.37 (dd,1H); 6.42 (d, 1H); 6.90–7.30 (m,9H); 8.0 (bs,1H). |

EXAMPLE 34

3-(4-Fluorophenyl)-5-isopropyl-1,2-diphenyl-pyrrole

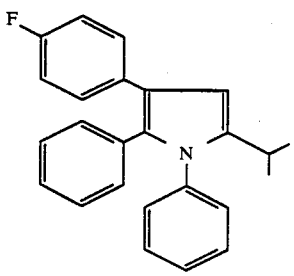

10.1 g (34 mmol) of 2-(4-fluorophenyl)-5-methyl-1-phenyl-hexane-1,4-dione (Example 2) and 9.3 mmol (102 mmol) of aniline in 150 ml of toluene are heated under reflux in a water separator for 24 hours with the addition of 500 mg of p-toluenesulphonic acid. After cooling and diluting with ethyl acetate, the reaction mixture is washed with 1 N hydrochloric acid and then with sodium bicarbonate solution, dried over magnesium sulphate and concentrated in vacuo. The residue is then chromatographed on silica gel.

Yield: 4.4 g (37% of theory).

¹H-NMR (CDCl₃): =1.17 (d, 6H); 2.70 (septet., 1H); 6.28 (s, 1H); 6.80 - 7.30 (m, 14H).

The compounds shown in Table 2 were obtained analogously to Example 6 and the reactions described in Examples 1, 2, 33,4 and 5.

TABLE 2

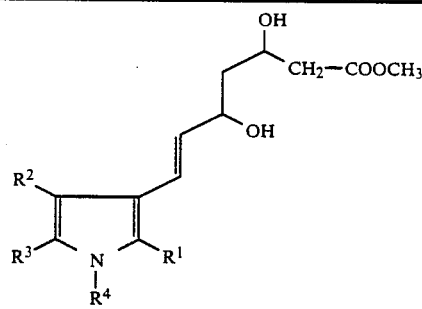

| Ex. No. | R¹ | R² | R³ | R⁴ | ¹H-NMR [δ ppm, CDCl₃, 300 MHz] |
|---|---|---|---|---|---|
| 35 | —CH(CH₃)₂ | ⌬—F | ⌬ | ⌬ | 1.27 (d,6H); 1.47 (m,1H); 1.60 (m,1H); 2.47 (m,2H); 2.97 (sept.,1H); 3.72 (s, 3H); 4.20 (m,1H); 4.38 (m,1H); 5.21 (dd, (1H); 5.75 (d,1H); 6.80–7.40 (m,14H). |
| 36 | —CH(CH₃)₂ | ⌬—F | ⌬ | ⌬—Cl | 1.27 (d,6H); 1.55 (m,2H); 2.48 (m,2H); 2.95 (sept.,1H); 3.72 (s,3H); 4.19 (m, 1H); 4.38 (m,1H); 5.20 (dd,1H); 6.73 (d, 1H); 6.80–7.30 (m,13H). |

TABLE 2-continued

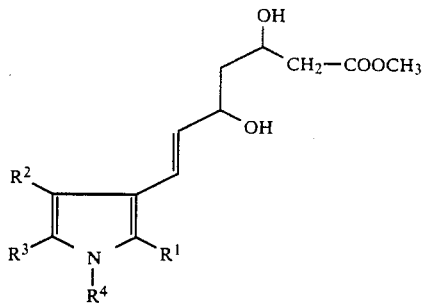

| Ex. No. | R¹ | R² | R³ | R⁴ | ¹H-NMR [δ ppm, CDCl₃, 300 MHz] |
|---|---|---|---|---|---|
| 37 | —CH(CH₃)₂ | 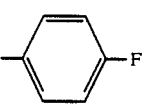 4-F-phenyl | 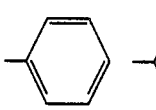 phenyl | 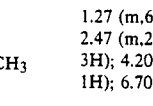 4-CH₃-phenyl | 1.27 (m,6H); 1.60 (m,2H); 2.33 (s,3H); 2.47 (m,2H); 3.02 (sept.,1H); 3.72 (s, 3H); 4.20 (m,1H); 4.41 (m,1H); 5.21 (dd, 1H); 6.70–7.30 (m,14H). |
| 38 | —CH(CH₃)₂ | 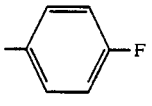 4-F-phenyl | 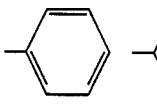 phenyl | 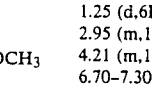 4-OCH₃-phenyl | 1.25 (d,6H); 1.55 (m,2H); 2.47 (m,2H); 2.95 (m,1H); 3.72 (s,3H); 3.78 (s,3H); 4.21 (m,1H); 4.38 (m,1H); 5.20 (dd,1H); 6.70–7.30 (m,14H). |
| 39 | —CH(CH₃)₂ | 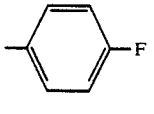 4-F-phenyl | 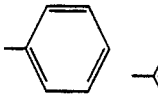 phenyl | 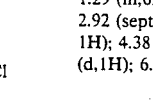 3,4-diCl-phenyl | 1.29 (m,6H); 1.45 (m,1H); 2.47 (m,2H); 2.92 (sept.,1H); 3.72 (s,3H); 4.18 (m, 1H); 4.38 (m,1H); 5.20 (dd,1H); 6.69 (d,1H); 6.80–7.30 (m,12H). |
| 40 | —CH(CH₃)₂ | 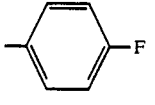 4-F-phenyl | 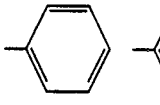 phenyl | 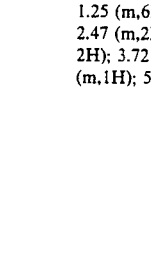 2-benzyl-phenyl | 1.25 (m,6H); 1.45 (m,1H); 1.60 (m,1H); 2.47 (m,2H); 2.76 (sept.,1H); 3.42 (m, 2H); 3.72 (s,3H); 4.18 (m,1H); 4.38 (m,1H); 5.19 (m,1H); 6.70–7.45 (m,19H). |
| 41 | —CH(CH₃)₂ | 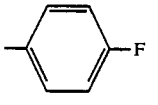 4-F-phenyl | 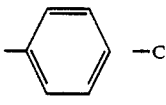 phenyl | —CH₂—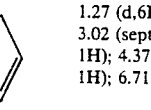 | 1.27 (d,6H); 1.55 (m,2H); 2.47 (m,2H); 3.02 (sept.,1H); 3.72 (s,3H); 4.20 (m, 1H); 4.37 (m,1H); 5.05 (s,2H); 5.16 (dd, 1H); 6.71 (d,1H); 6.80–7.30 (m,14H). |
| 42 | —CH(CH₃)₂ | 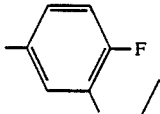 2-F-5-phenoxy-phenyl | 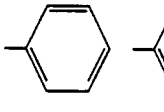 phenyl | 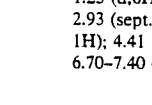 phenyl | 1.23 (d,6H); 1.55 (m,2H); 2.47 (m,2H); 2.93 (sept.,1H); 3.72 (s,3H); 4.24 (m, 1H); 4.41 (m,1H); 5.30 (dd,1H); 6.70–7.40 (m,19H). |

EXAMPLE 43

2-(4-Fluorophenyl)-1,5-dimethyl-hexane-1,4-dione

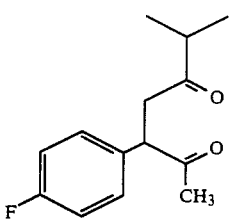

A solution of 7.9 g (0.05 mol) of 1,5-diazabicyclo(5,4,-0)undec-5-ene in 50 ml of acetonitrile is added dropwise at 0° C. to a solution of 19.2 g (0.1 mol) of 1-(4-fluorophenyl)-4-methyl-pent-1-en-3-one and 8.6 ml (0.12 mol) of nitroethane in 100 ml of acetonitrile. The mixture is then stirred at room temperature for 3 hours and 100 ml of 0.5 N hydrochloric acid are added. After extraction with methylene chloride, the organic phase is dried using sodium sulphate and concentrated. The oily residue is dissolved in 100 ml of ethanol and a solution of 4.8 g (0.12 mol) of sodium hydroxide in 60 ml of water is added at room temperature. This reaction solution is then added dropwise with ice cooling to a solution of 13.3 ml (0.25 mol) of concentrated sulphuric acid in 100 ml of water. After stirring for 0.5 hours at room temperature, the mixture is diluted with water and extracted several times with ether. The organic phase is washed twice each with 0.5 N hydrochloric acid and saturated sodium bicarbonate solution, dried over magnesium sulphate, concentrated in vacuo and the residue is chromatographed on silica gel.

Yield: 14.7 g (62.3% of theory).

$^1$H-NMR (CDCl$_3$): δ=1.07 (d, 3H); 1.12 (d, 3H); 2.13 (s, 3H); 2.60 (m, 2H); 3.42 (dd, 1H); 4.24 (dd, 1H); 7.00–7.30 (m, 4H).

The compounds shown in Table 3 were obtained analogously to Example 6 and the reactions described in Examples 1, 43, 3 or 34, 4 and 5.

TABLE 3

| Ex. No. | R$^1$ | R$^2$ | R$^3$ | R$^4$ | $^1$H-NMR [δ ppm, CDCl$_3$, 300 MHz] |
|---|---|---|---|---|---|
| 44 | —CH(CH$_3$)$_2$ | 4-F-phenyl | —CH$_3$ | —CH$_3$ | 1.37 (d,6H); 1.55 (m,2H); 2.09 (s,3H); 2.47 (m,2H); 3.30 (m,1H); 3.52 (s,3H); 3.72 (s,3H); 4.20 (m,1H); 4.33 (m,1H); 5.12 (dd,1H); 6.53 (d,1H); 6.90–7.20 (m,4H). |
| 45 | —CH(CH$_3$)$_2$ | 4-F-phenyl | —CH$_3$ | phenyl | 1.20 (d,6H); 1.55 (m,2H); 1.82 (s,3H); 2.47 (m,2H); 2.87 (sept.,1H); 3.72 (s, 3H); 4.18 (m,1H); 4.37 (m,1H); 5.18 (dd, 1H); 6.68 (d,1H); 6.90–7.50 (m,9H). |
| 46 | —CH(CH$_3$)$_2$ | 4-F-phenyl | —CH$_3$ | benzylphenyl | 1.18 (d,3H); 1.28 (d,3H); 1.50–1.60 (m,5H); 2.47 (m,2H); 2.69 (sept.,1H); 3.63 (m,2H); 3.72 (s,3H); 4.19 (m,1H); 4.37 (m,1H); 5.17 (dd,1H); 6.71 (d,1H); 7.00–7.50 (m,13H). |
| 47 | —CH(CH$_3$)$_2$ | 2-F-3-phenoxyphenyl | —CH$_3$ | —CH$_3$ | 1.32 (d,6H); 1.55 (m,2H); 2.08 (s,3H); 2.47 (m,2H); 3.28 (sept.,1H); 3.48 (s, 3H); 3.72 (s,3H); 4.20 (m,1H); 4.33 (m, 1H); 5.19 (dd,1H); 6.50 (d,1H); 6.90–7.40 (m,8H). |

TABLE 3-continued

[Structure: pyrrole with R1, R2, R3, R4 substituents and CH=CH-CH(OH)-CH2-CH(OH)-CH2-COOCH3 side chain]

| Ex. No. | R¹ | R² | R³ | R⁴ | ¹H-NMR [δ ppm, CDCl₃, 300 MHz] |
|---|---|---|---|---|---|
| 48 | —CH(CH₃)₂ | [3-phenoxy-4-fluorophenyl] | —CH₃ | [phenyl] | 1.18 (d,6H); 1.55 (m,2H); 1.80 (s,3H); 2.47 (m,2H); 2.85 (sept.,1H); 3.72 (s, 3H); 4.23 (m,1H); 4.38 (m,1H); 5.26 (dd, 1H); 6.63 (d,1H); 7.00–7.50 (m,13H). |

EXAMPLE 49

Methyl erythro-(E)-7-[3-(4-fluorophenyl)-5-isopropyl-1-methyl-2-phenyl-pyrrol-4-yl]-3,5-dihydroxy-heptanoate

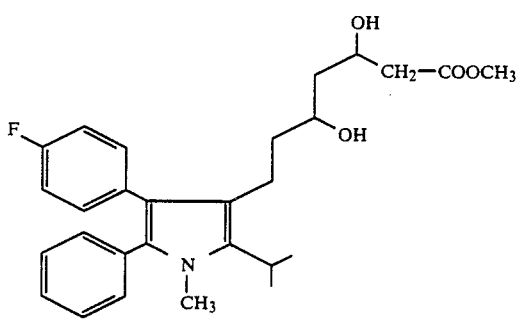

100 mg of the compound from Example 6 are dissolved in 20 ml of methanol and 10 μl of triethylamine and, after addition of 15 mg of 10% strength palladium on animal charcoal, the mixture is hydrogenated for 3.5 hours at 2.5 bar. The catalyst is removed by filtration and the solution is concentrated in vacuo.

Yield: 91 mg (90% of theory).

¹H-NMR (CDCl₃): δ=1.45 (m, 10H); 2.48 (m, 2H); 2.60 (m, 2H); 2.97 (m, 1H); 3.28 (m, 1H); 3.49 (s, 3H); 3.70 (s, 3H); 4.12 (m, 1H); 6.80–7.30 (m, 9H).

USE EXAMPLE

EXAMPLE 50

The determination of the enzyme activity was carried out by a modification of the method of G. C. Ness et al., Archives of Biochemistry and Biophysics 197, 493–499 (1979). Male Rico rats (body weight 300–400 g) were treated for 11 days with altromin powdered food to which 40 g of cholestyramine/kg of food had been added. After decapitation, the livers were removed from the animals and placed on ice. The livers were comminuted and homogenized 3 times in 3 volumes of 0.1M sucrose, 0.05M KCl, 0.04M $K_xH_y$ phosphate (mixture of $K_2HPO_4$ and $KH_2PO_4$ with a PH of 7.2), 0.03M ethylenediaminetetraacetic acid, 0.002M dithiothreitol (SPE) buffer (sucrose/phosphate/ethylenediaminetetraacetic acid buffer) pH 7.2 in a Potter-Elvejem homogenizer. The mixture was then centrifuged for 15 minutes and the sediment was discarded. The supernatant was sedimented at 100,000 g for 75 minutes. The pellet is taken up in ¼ volume of SPE buffer, homogenized again and then centrifuged again for 60 minutes. The pellet is taken up in 5 times its volume of SPE buffer, homogenized and frozen and stored at −78° C. (=enzyme solution).

For testing, the test compounds (and mevinolin as a reference substance) were dissolved in dimethylformamide with the addition of 5% by volume of 1N NaOH, and were used in the enzyme test in an amount of 10 μl in various concentrations. The test was started after preincubation of the compounds with the enzyme at 37° C. for 20 minutes. The test batch was 0.380 ml and contained 4 μmol glucose 6-phosphate, 1.1 mg bovine serum albumin, 2.1 μmol of dithiothreitol, 0.35 μmol of NADP (β-Nicotinamide-adenine-dinucleotide-phosphate), 1 unit of glucose 6-phosphate dehydrogenase, 35 μmol of $K_xH_y$ phosphate pH 7.2, 20 βl of enzyme preparation and 56 nmol of 3-hydroxy-3-methyl-glutaryl coenzyme A (glutaryl-3-¹⁴C) 100,000 dpm.

The mixture was incubated at 37° C. for 60 minutes and the reaction was stopped by addition of 300 μl of 0.24M HCl. After post-incubation of 60 minutes at 37° C., the batch was centrifuged and 600 μl of the supernatant were applied to a 0.7×4 cm column filled with 5-chloride anion exchanger of grain size 100 to 200 mesh. The column was rinsed with 2 ml of distilled water, 3 ml of a scintillation liquid were added to the eluate plus wash water and the mixture was counted in a scintillation counter. The IC₅₀ values were determined by interpolation by plotting the percentage inhibition against the concentration of the compound in the test.

To determine the relative inhibitory potency, the IC₅₀ value of the reference substance mevinolin was set at 100 and compared with the IC₅₀ value determined simultaneously for the test compound.

The compounds of invention have a higher inhibitory potency than mevinolin.

EXAMPLE 51

The subchronic action of the compounds according to the invention on blood cholesterol levels in dogs was tested in feeding experiments lasting several weeks. For this purpose, the substance to be investigated was administered once daily p.o. together with the feed in a capsule over a period of several weeks to healthy beagle hounds. In addition, cholestyramine (4 g/100 g of feed) as a bile acid sequesterant was mixed with the feed over the entire experimental period, i.e. before, during and after the administration period of the substance to be investigated. Venous blood was taken from the dogs twice weekly, and the serum cholesterol was determined enzymatically. The serum cholesterol levels during the period of administration were compared to the serum cholesterol levels before the administration period (control).

For the active compound according to Example 6, for example, the serum cholesterol was reduced by 27% after administration for 2 weeks at a level of 2 mg/kg p.o. daily.

It is understood that the specification and examples are illustrative but not limitative of the present invention and that other embodiments within the spirit and scope of the invention will suggest themselves to those skilled in the art.

We claim:
1. A substituted pyrrole of the formula:

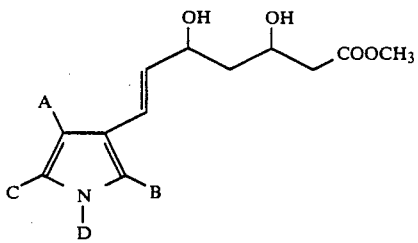

wherein
(1)
A represents a member selected from the group consisting of 4-fluorophenyl, phenyl, 4-chlorophenyl, 4-methylphenyl, 4-methoxyphenyl, 2-fluorophenyl, 2,4-difluorophenyl, 4-fluoro-2-methylphenyl, and 4-fluoro-3-phenoxyphenyl,
B represents isopropyl,
C represents phenyl, and
D represents methyl;
(2)
A represents 4-fluorophenyl,
B represents cyclopropyl,
C represents phenyl, and
D represents methyl;
(3)
A represents 4-fluorophenyl,
B represents isopropyl,
C represents a member selected from the group consisting of 4-chlorophenyl, 4-fluorophenyl, and 3-benzyloxyphenyl, and
D represents methyl;
(4)
A represents phenyl,
B represents isopropyl,
C represents a member selected from the group consisting of 3-(4-fluorobenzyloxy)phenyl and 3-(3-fluorobenzyloxy)phenyl, and
D represents methyl;
(5)
A represents 4-fluorophenyl,
B represents isopropyl,
C represents phenyl, and
D represents a member selected from the group consisting of ethyl, isopropyl, hydrogen, phenyl, 4-chlorophenyl, 4-methylphenyl, 4-methoxyphenyl, 3,4-dichlorophenyl, 2-benzylphenyl, and benzyl;
(6)
A represents 4-fluoro-3-phenoxyphenyl,
B represents isopropyl,
C represents phenyl, and
D represents phenyl;
(7)
A represents 4-fluorophenyl,
B represents isopropyl,
C represents methyl, and
D represents a member selected from the group consisting of methyl, phenyl and 2-benzylphenyl;
(8)
A represents 4-fluoro-3-phenoxyphenyl,
B represents isopropyl,
C represents methyl, and
D represents a member selected from the group consisting of methyl and phenyl; and
(9)
A represents isopropyl,
B represents 4-fluorophenyl,
C represents methyl, and
D represents a member selected from the group consisting of phenyl, 2,6-dimethylphenyl and benzyl.

2. A compound according to claim 1, wherein such compound is methyl 7-[3-(4-fluoro-3-phenoxy-phenyl)-5-isopropyl-1-methyl-2-phenyl-pyrrol-4-yl]-3-5-dihydroxy-hept-6-enoate of the formula

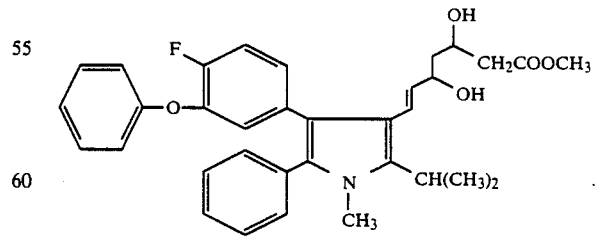

3. A compound according to claim 1, wherein such compound is methyl erythro-(E)-7-[3-(4-fluorophenyl)-5-isopropyl-1-ethyl-2-phenyl-pyrrol-4yl]-3,5-dihydroxy-hept-6-enoate of the formula 4. A compound according to claim 1, wherein such compound is methyl erythro-(E)-7-[3-(4-fluorophenyl)-5-isopropyl-1-isopropyl-2-phenyl-pyrrol-4-yl]-3,5-dihydroxy-hept-6-enoate of the formula

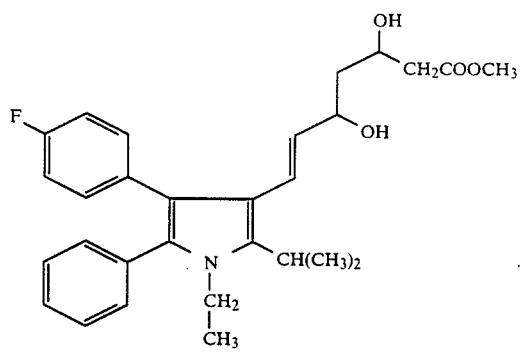

5. A compound according to claim 1, wherein such compound is methyl erythro-(E)-7-[3-(4-fluorophenyl)-5-isopropyl-1-phenyl-2-phenyl-pyrrol-4yl]-3,5-dihydroxy-hept-6-enoate of the formula

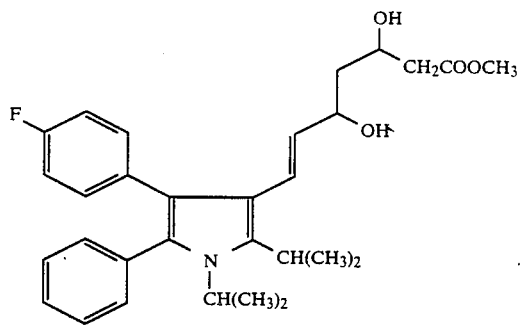

6. A compound according to claim 1, wherein such compound is methyl erythro-(E)-7-[3-(4-fluorophenyl)-5-isopropyl-1-(4-methyl-phenyl)-2-phenyl-pyrrol-4yl]-3,5-dihydroxy-hept-6-enoate of the formula

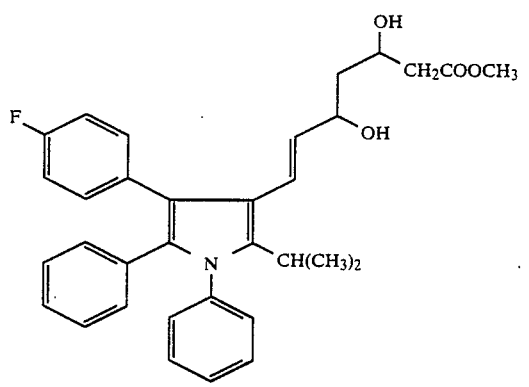

7. A compound according to claim 1, wherein such compound is methyl erythro-(E)-7-[3-(4-fluorophenyl)-5-isopropyl-1-phenyl-2-methyl-pyrrol-4-yl]-3,5-dihydroxy-hept-6-enoate of the formula

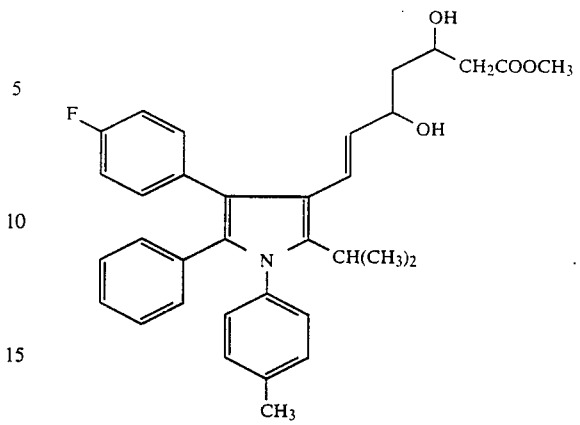

8. A compound according to claim 1, wherein such compound is methyl erythro-(E)-7-[3-(4-fluorophenyl)-5-isopropyl-1-(2-benzyl-phenyl)-2-methyl-pyrrol-4-yl]-3,5-dihydroxy-hept-6-enoate of the formula

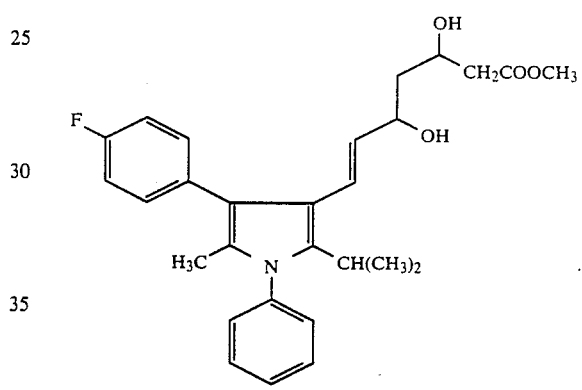

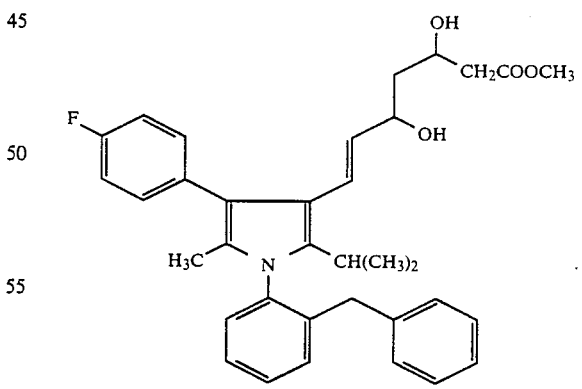

9. A composition for inhibiting 3-hydroxy-3-methylglutaryl coenzyme A (HMG-CoA) reductase comprising an amount effective therefor of a substituted pyrrole according to claim 1 and a diluent.

* * * * *